(12) United States Patent
Bernard et al.

(10) Patent No.: US 10,260,685 B2
(45) Date of Patent: Apr. 16, 2019

(54) LED LAMP WITH AROMATIC STRUCTURE

(71) Applicant: Cree, Inc., Durham, NC (US)

(72) Inventors: Randall Levy Bernard, Cary, NC (US); P. Joseph DeSena, Jr., Raleigh, NC (US); Philip Scott, Honeoye Falls, NY (US)

(73) Assignee: Cree, Inc., Durham, NC (US)

( * ) Notice: Subject to any disclaimer, the term of this patent is extended or adjusted under 35 U.S.C. 154(b) by 68 days.

(21) Appl. No.: 15/427,568

(22) Filed: Feb. 8, 2017

(65) Prior Publication Data

US 2018/0224072 A1  Aug. 9, 2018

(51) Int. Cl.

| | |
|---|---|
| *F21V 29/77* | (2015.01) |
| *A61L 9/02* | (2006.01) |
| *F21V 17/10* | (2006.01) |
| *F21K 9/237* | (2016.01) |
| *F21K 9/235* | (2016.01) |
| *F21V 29/83* | (2015.01) |
| *F21K 9/232* | (2016.01) |
| *F21V 23/00* | (2015.01) |
| *F21V 29/85* | (2015.01) |
| *F21V 33/00* | (2006.01) |
| *F21Y 115/10* | (2016.01) |

(52) U.S. Cl.
CPC .............. *F21K 9/237* (2016.08); *A61L 9/02* (2013.01); *F21K 9/232* (2016.08); *F21K 9/235* (2016.08); *F21V 23/005* (2013.01); *F21V 29/77* (2015.01); *F21V 29/83* (2015.01); *F21V 29/85* (2015.01); *F21V 33/0024* (2013.01); *F21V 17/10* (2013.01); *F21Y 2115/10* (2016.08)

(58) Field of Classification Search
CPC .......... F21K 9/232; F21K 9/235; F21K 9/237; F21K 9/238; A61L 9/02; A61L 9/03; A61L 2209/12; H01K 7/00; H01K 7/02; H01K 7/04; H01K 7/06; F21S 8/02; F21S 8/026; F21V 29/77; F21V 29/83; F21V 29/85; F21V 23/005; F21V 33/0024; F21V 17/10
USPC ............................................ 362/96; 422/125
See application file for complete search history.

(56) References Cited

U.S. PATENT DOCUMENTS

| | | | |
|---|---|---|---|
| 7,213,940 B1 | 5/2007 | Van De Ven et al. | |
| 7,484,860 B2 * | 2/2009 | Demarest | A01M 1/2083 362/253 |
| 2004/0231360 A1 * | 11/2004 | Lagardere | A44C 1/00 63/1.13 |
| 2008/0130266 A1 * | 6/2008 | DeWitt | A61L 9/03 362/96 |
| 2013/0012680 A1 * | 1/2013 | Hamaguchi | C08G 63/605 528/193 |
| 2016/0051719 A1 * | 2/2016 | Watanabe | A61L 9/205 422/121 |
| 2016/0102855 A1 * | 4/2016 | Kowalchuk | F21V 33/0004 362/154 |

* cited by examiner

*Primary Examiner* — Alan B Cariaso
(74) *Attorney, Agent, or Firm* — Myers Bigel, P.A.

(57) ABSTRACT

An LED lamp includes a LED assembly comprising at least one LED operable to emit light when energized through an electrical path. A heat sink structure is thermally coupled to the LED assembly for dissipating heat to the ambient environment. An aromatic structure is thermally coupled to the heat sink structure such that the aromatic structure is heated by the heat dissipated from the heat sink.

19 Claims, 24 Drawing Sheets

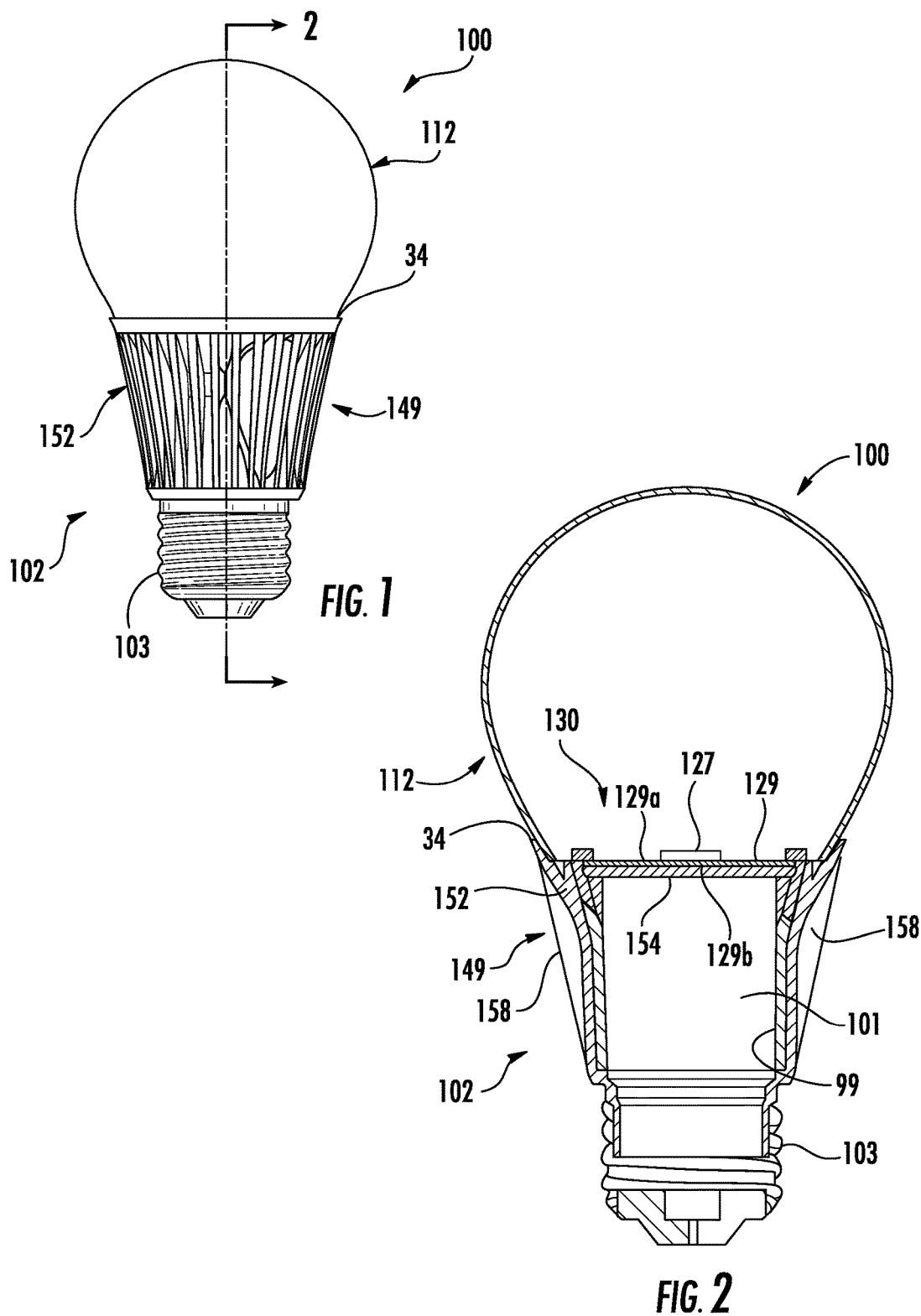

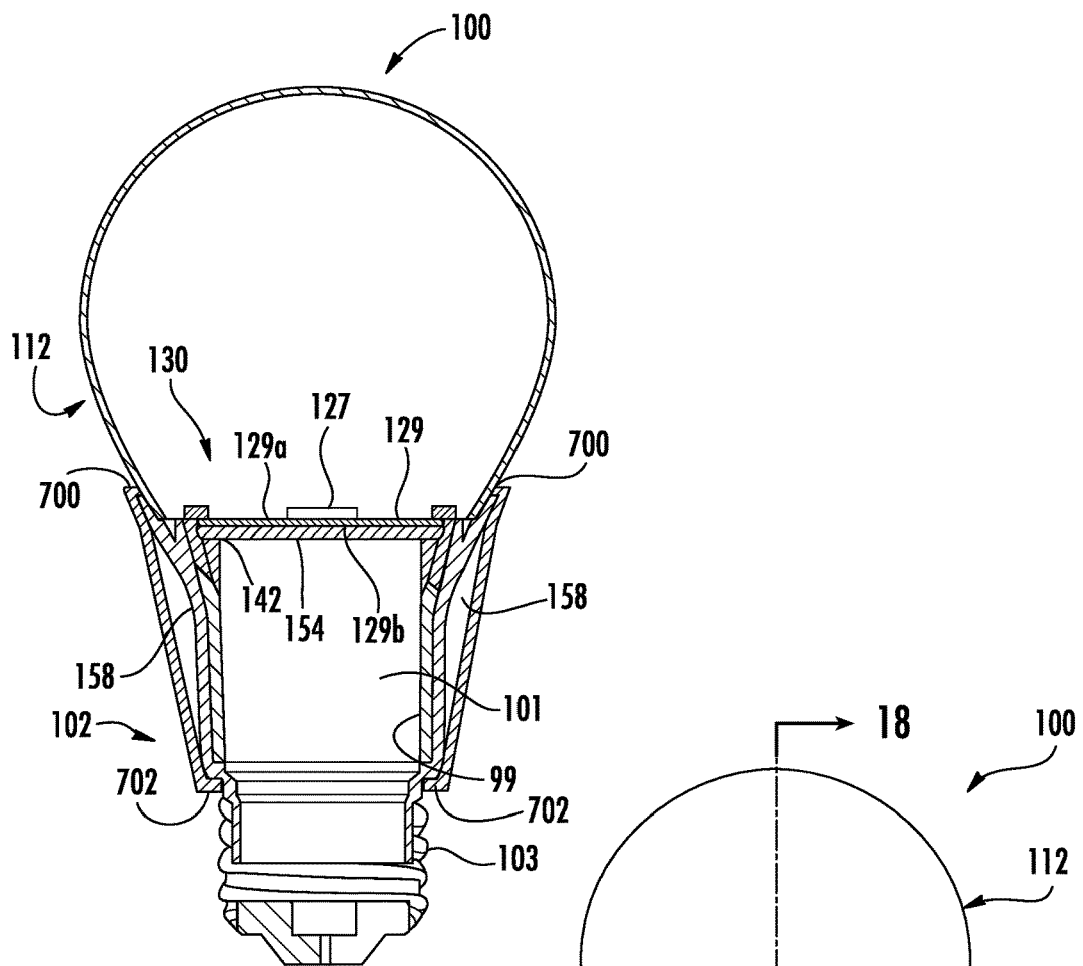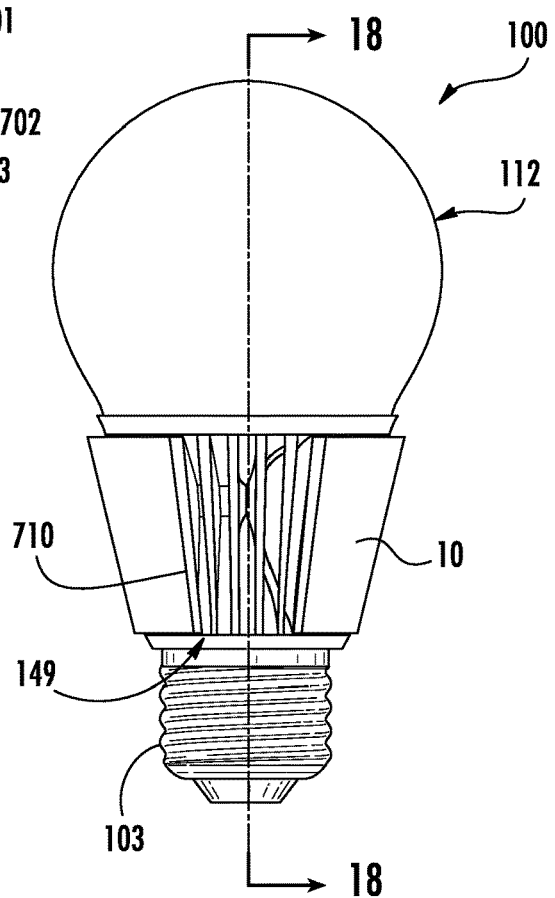
FIG. 18
FIG. 19

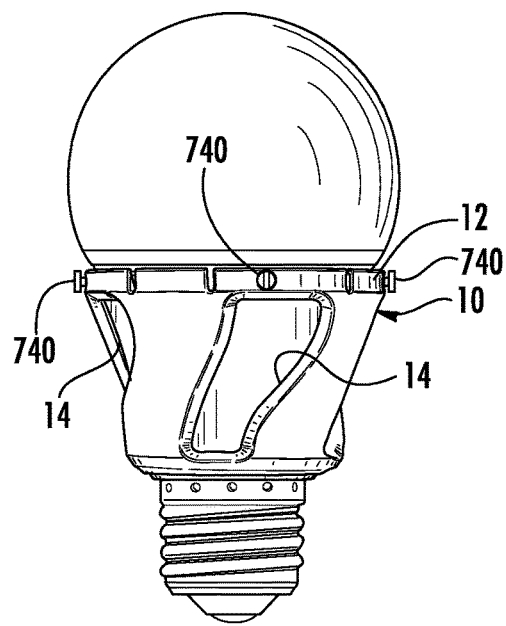 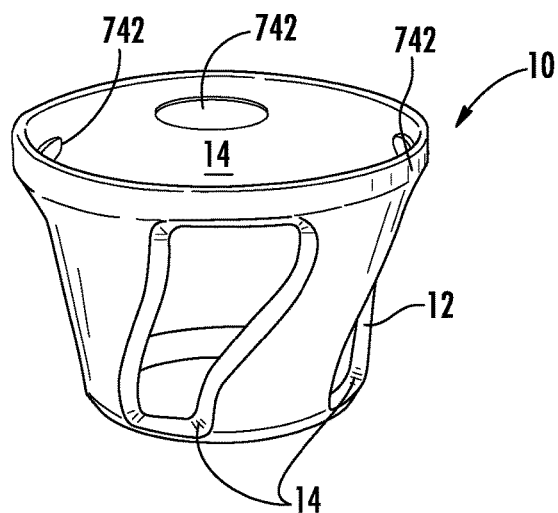
FIG. 22   FIG. 23
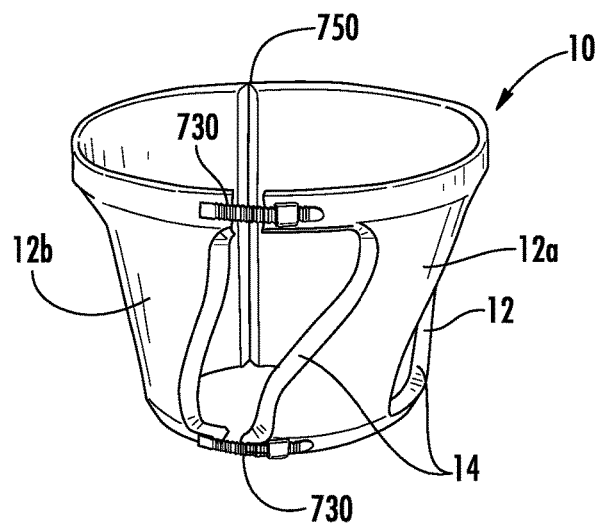
FIG. 24

LED LAMP WITH AROMATIC STRUCTURE

BACKGROUND

Light emitting diode (LED) lighting systems are becoming more prevalent as replacements for older lighting systems. LED systems are an example of solid state lighting (SSL) and have advantages over traditional lighting solutions such as incandescent and fluorescent lighting because they use less energy, are more durable, operate longer, can be combined in multi-color arrays that can be controlled to deliver virtually any color light, and generally contain no lead or mercury. A solid-state lighting system may take the form of a lighting unit, light fixture, light bulb, or a "lamp."

An LED lighting system may include, for example, a packaged light emitting device including one or more light emitting diodes (LEDs), which may include inorganic LEDs, which may include semiconductor layers forming p-n junctions and/or organic LEDs (OLEDs), which may include organic light emission layers. Light perceived as white or near-white may be generated by a combination of red, green, and blue ("RGB") LEDs. Output color of such a device may be altered by separately adjusting supply of current to the red, green, and blue LEDs. Another method for generating white or near-white light is by using a lumiphor such as a phosphor. Still another approach for producing white light is to stimulate phosphors or dyes of multiple colors with an LED source. Many other approaches can be taken.

An LED lamp may be made with a form factor that allows it to replace a standard incandescent bulb, or any of various types of fluorescent lamps. LED lamps often include some type of optical element or elements to allow for localized mixing of colors, collimate light, or provide a particular light pattern. Sometimes the optical element also serves as an envelope or enclosure for the electronics and/or the LEDs in the lamp. LED lamps may also take the form factor of a downlight "can" light, troffer-style fixture or the like.

A power supply may be included in or with the lamp structure along with the LEDs or LED packages and the optical components. A heat sink is also often needed to cool the LEDs and/or power supply in order to maintain appropriate operating temperature.

SUMMARY OF THE DISCLOSURE

In some embodiments, a LED lamp comprises a LED assembly comprising at least one LED operable to emit light when energized through an electrical path. A heat sink structure is thermally coupled to the LED assembly for dissipating heat to the ambient environment. An aromatic structure is in close proximity to the heat sink structure such that the aromatic structure is heated by the heat dissipated from the heat sink structure.

The aromatic structure may comprise a plastic infused with an aromatic material. The aromatic structure may be removably mounted to the lamp. The aromatic structure may be removably attached to the lamp using at least one of a snap-fit connector, a friction fit and an adjustable strap. The aromatic structure may comprise apertures allowing the heat sink structure access to the ambient environment. The aromatic structure may be permanently attached to the heat sink structure. The aromatic structure may form part of the heat sink structure.

In some embodiments a LED lamp comprises a LED assembly comprising at least one LED operable to emit light when energized through an electrical path. A heat sink structure is thermally coupled to the LED assembly for dissipating heat to the ambient environment. An aromatic structure has an interior surface that contacts the heat sink structure such that the aromatic structure is heated by the heat dissipated from the heat sink structure.

The aromatic structure may comprise a plastic infused with an aromatic material. The aromatic structure may be removably mounted to the lamp. The aromatic structure may be removably attached to the lamp using at least one of a snap-fit connector, a friction fit and an adjustable strap. The aromatic structure may comprise apertures allowing the heat sink structure access to the ambient environment. The aromatic structure may be permanently attached to the heat sink. The aromatic structure may be molded to the heat sink. The aromatic structure may comprise a trim ring.

In some embodiments a LED lamp comprises a LED assembly comprising at least one LED operable to emit light when energized through an electrical path. A heat sink structure is thermally coupled to the LED assembly for dissipating heat to the ambient environment. The heat sink structure may comprise thermally conductive plastic infused with an aromatic substance such that the aromatic substance is dispersed by the heat dissipated from the heat sink structure.

In some embodiments an aromatic structure for an LED lamp comprises a shell configured to fit at least partially over a heat sink of a LED lamp. The shell comprising a plastic infused with an aromatic material. The shell may comprise at least one of a snap-fit connector, an adjustable strap, a screw connection and an elastic strap. In some embodiments an aromatic structure for an LED lamp comprises a trim ring configured to attach to a LED lamp. The trim ring comprises a plastic infused with an aromatic material. The trim ring may comprise at least one of a spring clip, screw and deformable connector.

BRIEF DESCRIPTION OF THE DRAWINGS

FIG. 1 is a side view of an embodiment of an exemplary LED lamp in which the invention may be used.

FIG. 2 is a section view along section line 1B-1B of FIG. 1.

FIG. 18 is a section view of the lamp of FIG. 1 with another embodiment of the aromatic structure of the invention attached to the lamp.

FIG. 19 is a side view of the lamp of FIG. 1 with yet another embodiment of the aromatic structure of the invention attached to the lamp.

FIGS. 20, 21, 23 and 24 are perspective views of other embodiments of the aromatic structure of the invention.

FIG. 22 is a side view of another embodiment of the aromatic structure of the invention mounted on the lamp of FIG. 4.

DETAILED DESCRIPTION

Figure 3:
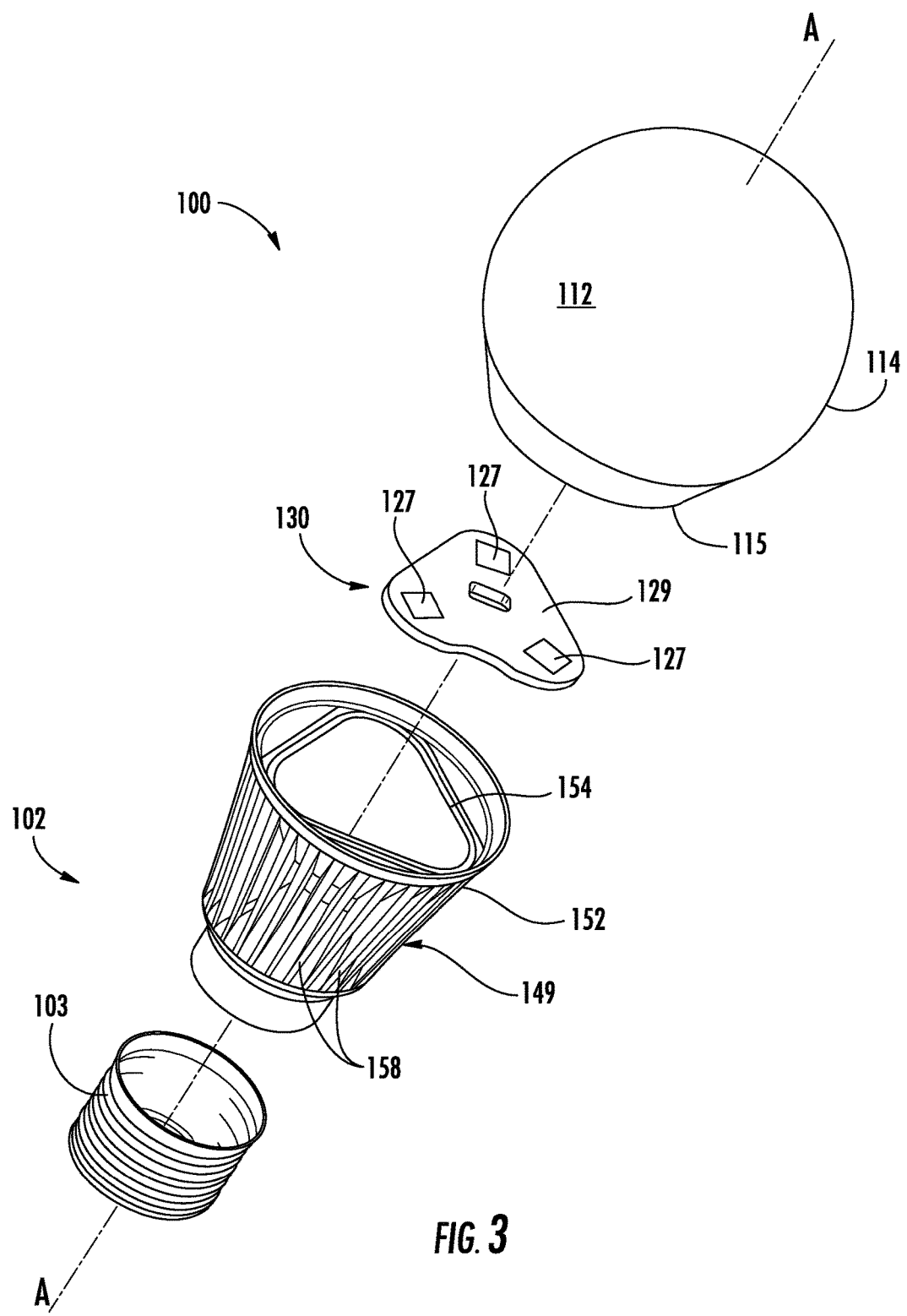
FIG. 3 is an exploded perspective view the lamp of FIG. 1.

Embodiments of the present disclosure now will be described more fully hereinafter with reference to the accompanying drawings, in which embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like numbers refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" or "top" or "bottom" may be used herein to describe a relationship of one element, layer or region to another element, layer or region as illustrated in the figures. It will be understood that these terms are intended to encompass different orientations of the device in addition to the orientation depicted in the figures.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Unless otherwise expressly stated, comparative, quantitative terms such as "less" and "greater", are intended to encompass the concept of equality. As an example, "less" can mean not only "less" in the strictest mathematical sense, but also, "less than or equal to."

The terms "LED" and "LED device" as used herein may refer to any solid-state light emitter. The terms "solid state light emitter" or "solid state emitter" may include a light emitting diode, laser diode, organic light emitting diode, and/or other semiconductor device which includes one or more semiconductor layers, which may include silicon, silicon carbide, gallium nitride and/or other semiconductor materials, a substrate which may include sapphire, silicon, silicon carbide and/or other microelectronic substrates, and one or more contact layers which may include metal and/or other conductive materials. A solid-state lighting device produces light (ultraviolet, visible, or infrared) by exciting electrons across the band gap between a conduction band and a valence band of a semiconductor active (light-emitting) layer, with the electron transition generating light at a wavelength that depends on the band gap. Thus, the color (wavelength) of the light emitted by a solid-state emitter depends on the materials of the active layers thereof. In various embodiments, solid-state light emitters may have peak wavelengths in the visible range and/or be used in combination with lumiphoric materials having peak wavelengths in the visible range. Multiple solid state light emitters and/or multiple lumiphoric materials (i.e., in combination with at least one solid state light emitter) may be used in a single device, such as to produce light perceived as white or near white in character. In certain embodiments, the aggregated output of multiple solid-state light emitters and/or lumiphoric materials may generate warm white light output having a color temperature range of from about 2200K to about 6000K.

Solid state light emitters may be used individually or in combination with one or more lumiphoric materials (e.g., phosphors, scintillators, lumiphoric inks) and/or optical elements to generate light at a peak wavelength, or of at least one desired perceived color (including combinations of colors that may be perceived as white). Inclusion of lumiphoric (also called 'luminescent') materials in lighting devices as described herein may be accomplished by direct coating on solid state light emitter, adding such materials to encapsulants, adding such materials to lenses, by embedding or dispersing such materials within lumiphor support elements, and/or coating such materials on lumiphor support elements. Other materials, such as light scattering elements (e.g., particles) and/or index matching materials, may be associated with a lumiphor, a lumiphor binding medium, or a lumiphor support element that may be spatially segregated from a solid state emitter.

Embodiments of the invention may be used with a wide variety of LED lamps having different styles, configurations, and uses. The term "lamp" is meant to encompass not only a solid-state replacement for a traditional incandescent bulb as illustrated herein, but also replacements for fluorescent bulbs, replacements for complete fixtures such as downlights or troffer-style fixtures, and any type of light fixture that may be designed as a solid state lighting device. In some embodiments, a LED lamp comprises a base having an electrical connector. At least one LED is operable to emit light when energized through an electrical path from the base. A LED board is in the electrical path and supports the at least one LED. The LED board may be mounted on or be thermally coupled to a heat sink structure such that heat generated by the LEDs is dissipated from the lamp via the heat sink structure. The LED board may be mounted directly on the heat sink structure or it may be mounted in intervening elements such as a heat spreader that are in turn thermally coupled to the heat sink.

Referring to FIGS. 1-3, in one embodiment lamp 100 may be used as an A-series lamp, more particularly; lamp 100 is designed to serve as a solid-state replacement for an A19 incandescent bulb or similar bulbs. In one embodiment, the enclosure 112 and base 102 are dimensioned to be a replacement for an ANSI standard A19 bulb such that the dimensions of the lamp 100 fall within the ANSI standards for an A19 bulb. The dimensions may be different for other ANSI standards including, but not limited to, A21 and A23 standards. Moreover, the invention may be embodied in lamps of other styles and shapes including both standard and non-standard styles.

In some embodiments, the lamp comprises a base 102 and an optically transmissive enclosure 112. The base 102 may comprise an electrical connector such as an Edison screw 103 and a heat sink structure 149. The optically transmissive enclosure 112 surrounds the LED assembly 130 such that light is emitted from the lamp through the enclosure 112. LED assembly 130 comprises a LED board 129 physically supporting and forming part of the electrical path to the LEDs 127. The LED board 129 may be planar and extend transversely to the longitudinal axis A-A of the lamp as shown in FIGS. 2 and 3. The LED board 129 comprises a top surface 129a and an opposing bottom surface 129b. The bottom surface 129b is thermally coupled to heat sink structure 149. In some embodiments, the LEDs 127 are be arranged on the top surface 129a of LED board 129 to emit light primarily upwardly. In other embodiments the LED board and LEDs may be mounted on a tower that extends into the enclosure 112 where the tower may form part of or be thermally coupled to the heat sink. In such an embodiment the LEDs may emit light primarily laterally rather than upwardly. Additional components, such as ESDs, wires, via holes, contacts, coatings, etc., may be present in the LED assembly 130 or on the LED board 129 and its surfaces.

The LEDs 127 may be mounted on the exposed surface 129a of the LED board 129 and may emit light in a variety of patterns. The LED board 129 can be a metal core PCB, flex circuit, PCB or the like that is thermally coupled to the heat sink structure 149. If the LED board has structural rigidity it may be mounted directly to the heat sink structure; however, the LED board may be mounted on a supporting substrate such as a heat spreader that is in turn mounted on the heat sink structure 149. The figures depict a metal core PCB LED assembly 130 having three sides, however, other arrangements can be used, such as rectangular, square, pentagonal, circular, oval or irregular shapes.

The LEDs 127 may comprise an LED die disposed in an encapsulant such as silicone, and LEDs may be encapsulated with a phosphor and/or notch filter material to provide local wavelength conversion or wavelength filtering. A wide variety of LEDs and combinations of LEDs may be used. In at least some example embodiments, the LEDs are mounted on a LED board 129 to create a LED assembly 130 and are operable to emit light when energized through an electrical path from the base 102. In the present disclosure the term "LED board" is used to refer to the electronics board that supports the individual LEDs or LED packages and includes or supports electrical conductors that form part of the electrical path to deliver current to the LEDs.

An at least partially optically transmissive enclosure 112 is mounted to the base 102 for emitting light. The enclosure 112 may be connected to the base 102 by any suitable connection mechanism including adhesive, mechanical connectors, friction fit, separate fasteners or the like or combinations of such connection mechanisms. In some embodiments, the enclosure 112 may be made of glass, quartz, borosilicate, silicate, polycarbonate, other plastic or other suitable optically transmissive material. The enclosure 112 may be of similar shape to that commonly used in household incandescent bulbs. In some embodiments, the glass enclosure is coated on the inside with silica, providing a diffuse scattering layer that produces a more uniform far field pattern. The enclosure 112 may also be etched, frosted or coated. Alternatively, the surface treatment may be omitted and a clear enclosure may be provided.

The enclosure 112 may also be provided with a shatter proof or shatter resistant coating. It should also be noted that in this or any of the embodiments shown here, the optically transmissive enclosure 112 or a portion of the optically transmissive enclosure 112 could be coated or impregnated with phosphor or a diffuser. In an A19 style lamp, or in other bulbs having similar form factors, the enclosure 112 may have a traditional bulb shape having a globe shaped enclosure surface 114 that tapers to a narrower neck 115 and joins with base 102. In these embodiments, the enclosure may be entirely optically transmissive. In a lamp such as shown the light is emitted in an omnidirectional pattern and may be compliant with Energy Star® requirements for omnidirectional lamps. In some embodiments, components of the heat sink structure are positioned in the enclosure so as to spread and/or direct heat from the LEDs away from the power supply and the base.

The electrical connector, such as Edison screw 103, functions as the electrical and physical connector to connect the lamp 100 to an electrical socket or other connector. Depending on the embodiment, other base configurations are possible to make the electrical connection such as other standard bases or non-traditional bases. The Edison screw 103 may be connected to the heat sink structure 149 by adhesive, mechanical connector, welding, separate fasteners, soldered wires, or the like. The material of the heat sink structure 149 may comprise a thermally conductive material such that the heat sink structure dissipates heat from the lamp 100. The heat sink structure 149 and the Edison screw 103 define an internal cavity 99 for receiving the electronics of the lamp. The lamp electronics may be mounted on a lamp electronics board 101. The lamp electronics board 101 is electrically coupled to the Edison screw 103 such that an electrical connection may be made from the Edison screw 103 to the lamp electronics on lamp electronics board 101. The base 102 may be potted to physically and electrically isolate and protect the lamp electronics.

In some embodiments, the LED board 129 may be made of a thermally conductive material. Because in some embodiments the LED board 129 is pliable and the LED placement on the substrate may be varied, the LED board may be formed and bent into a variety of configurations. The orientation of the LEDs and the number of LEDs may be varied to create a desired light pattern. In other embodiments, the LED board may be manufactured in the desired shape.

In some embodiments, the lamp electronics such as a driver and/or power supply are included on the LED board 129. In other embodiments, the driver and/or power supply are included in the base 102 on the lamp electronics board 101. The power supply and drivers may also be mounted separately where components of the power supply are mounted in the base 102 and the driver is mounted with the LED board 129 in the enclosure 112. In some embodiments, the lamp electronics including a power supply and/or driver are mounted on a lamp electronics board where the board is supported in the base and is in the electrical path from the base to the LEDs.

The lamp electronics board may be electrically coupled by any suitable electrical connection to the electrical connector 103 of the base 102 such as by a soldered connection, wires or ribbons or direct contact between board contacts and the electrical connector 103. In some embodiments, the lamp electronics board may be mounted to extend vertically such that the lamp electronics board extends along or parallel to the longitudinal axis of the lamp. The lamp electronics board may be disposed at a substantially right angle to the transverse portion of the LED board 129. The LED board 129 may typically be mounted inside of the space of the enclosure 112 such that the LEDs 127 supported by the LED board 129 are positioned to emit light from the enclosure. An electrical connection can be made between the lamp electronics board 101 and the LED board 129 to complete the electrical path from the base to the LEDs 127.

The heat sink structure 149 may comprise a first LED mounting portion 154 for thermally coupling with the LED board 129, as well as an exposed heat dissipating portion 152 that extends externally of the lamp to dissipate heat to the ambient environment. In some embodiments, the LED mounting portion 154 and heat dissipating portion 152 may be comprised of separate or contiguous components configured to thermally engage with each other upon assembly. As shown in FIGS. 1-3, the heat dissipating portion 152 and the LED mounting portion 154 are separate components configured to thermally engage with each other. In this configuration, the heat dissipating portion 152 and the LED mounting portion 154 can be configured as a "cup and cap" where the LED mounting portion 154 and the heat dissipating portion 152 define cavity 99.

The LED mounting portion 154 is thermally coupled with the LED assembly 130 such that heat is conducted away from the LED assembly 130 by the LED mounting portion 154. The heat sink structure 149 comprises a heat dissipating portion 152 that may be in the form of a housing that also contains the lamp electronics and that dissipates the heat to the ambient environment. In one embodiment, the LED mounting portion 154 and the heat dissipating portion 152 are formed as two pieces where the LED mounting portion 154 fits into the heat dissipating portion 152 such that the LED mounting portion 154 separates the interior space of the enclosure 114 from the interior space 99 of the base 102.

The heat sink structure 149 and the LED mounting portion 154 for the LED board 129, may have a variety of configurations. The heat sink components may be made of metal such as aluminum or zinc or thermal plastic or other suitable thermally conductive material. In one embodiment, a plurality of heat dissipating members 158 may be formed on the exposed portions of the heat dissipating portion 152 to facilitate the heat transfer to the ambient environment. In one embodiment, the heat dissipating members 158 comprise a plurality fins that extend outwardly to increase the surface area of the heat sink. In some embodiments the heat sink structure 149 may be made of thermal plastic such that heat may be conducted to the ambient environment via the plastic heat sink, which may be of a thermal plastic or an engineering plastic or resin and/or a thermally conductive plastic or resin. In some embodiments, a portion of the heat sink assembly may be insert molded with the thermal plastic or an engineering plastic or resin and/or a thermally conductive plastic or resin.

Thermally conductive plastics (thermoplastics or thermosets) are generally not direct drop-in replacements for metals for heat management, but because of the conductive and convective heat flow pathways in such LED devices, nonetheless may allow replacement of metal with lighter weight material. In the present LED lamp configuration, in one aspect, conductivity-based heat management of the LED lamp may not be the limiting factor, and therefore, while metal may be the preferred material, it is not necessary. Moreover, thermally conductive plastics may provide a lower coefficient of thermal expansion (CTE) than metal, such as aluminum, as a heat sink source and can thereby reduce stresses due to differential expansion, as the thermally conductive plastics may more closely match the CTE of the LED element's construction (e.g., silicon, silicon carbide, sapphire or ceramics) that the thermally conductive plastic is in contact with. Most conductive plastics weigh 20-40% less than aluminum.

Examples of heat-conductive additives used in thermal conductive plastics are graphite carbon fibers and ceramics such as aluminum nitride and boron nitride. Graphite fibers conduct electricity as well as heat, whereas, ceramic additives are electrically insulative. Thermally conductive compounds may be compounded, combined or formulated with crystalline engineering resins such as polyamide, polyethersulphones, polysulphones, poly acetals, polycarbonates, polyether(ether)ketones, polyoxymethylene oxide, polyphenylene sulfide, polyphenylene oxide, liquid crystal polymers, and teflon due to their high heat resistance and lower melt viscosities, but amorphous resins or variants of the above can also be used.

Figure 4:
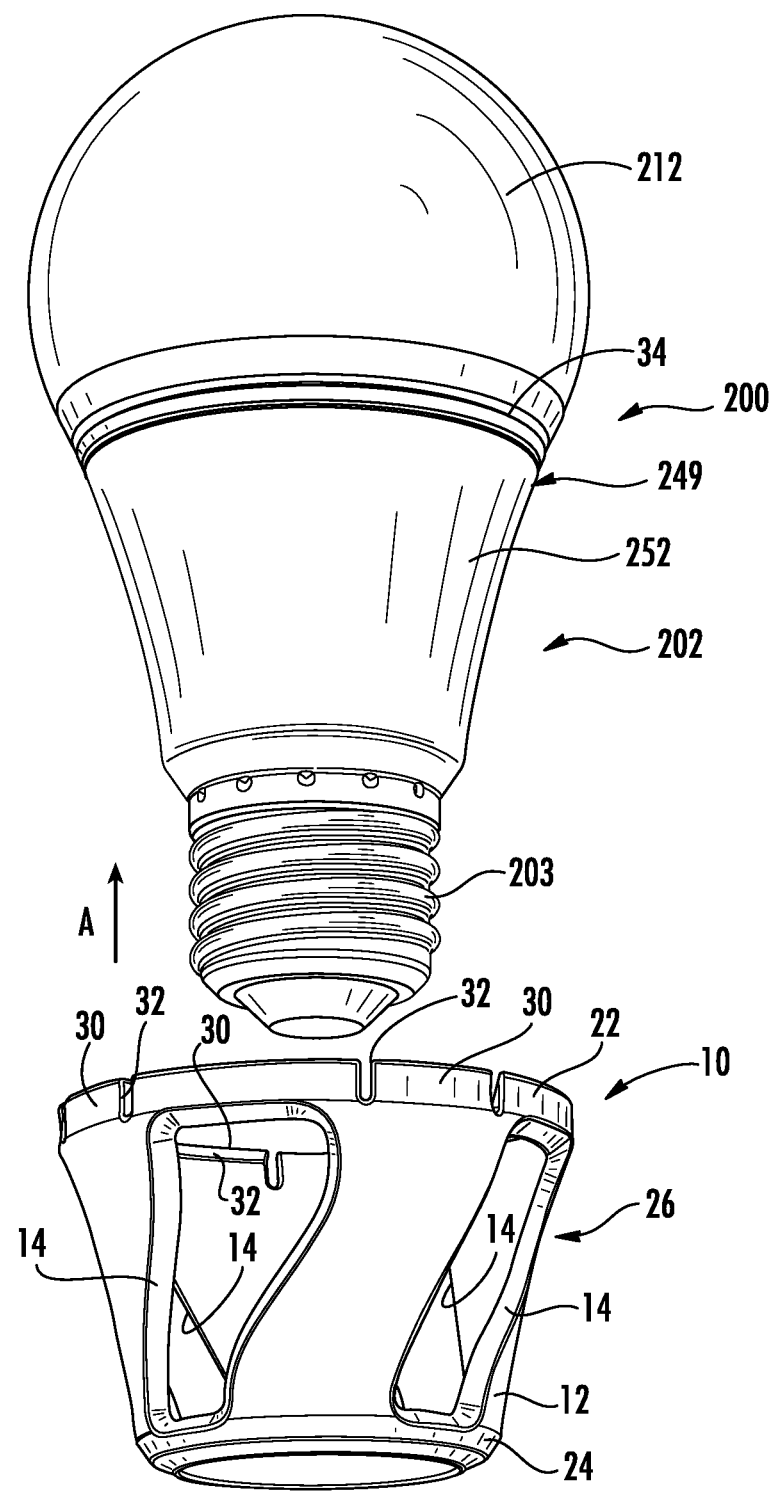
FIG. 4 is a perspective view of an embodiment of an exemplary LED lamp in which the invention may be used and an embodiment of the aromatic structure of the invention removed from the lamp.

Many configurations of the lamp and heat sink are possible for the lamp of the invention and the specific configurations of the lamp, the heat sink and the internal components as described herein are provided by way of example only. For example, FIG. 4 shows another embodiment of a LED lamp 200 having an at least partially optically transmissive enclosure 212 for emitting light from the lamp generated by LEDs (not shown) located internally of the enclosure. The base 202 comprises an electrical connector 203 in the form of an Edison screw and a heat dissipating portion 252 of the heat sink structure 249. In the embodiment of FIG. 4 the heat dissipating portion 252 has a smooth outer surface and does not include the fins 158 shown in the embodiment of FIGS. 1-3. The exposed heat dissipating portion 252 of the heat sink structure 249 may comprise multiple layers. For example, a metal shell may be surrounded by a plastic outer casing provided that sufficient heat is dissipated from the lamp that the performance of the LEDs is not degraded.

Figure 5:
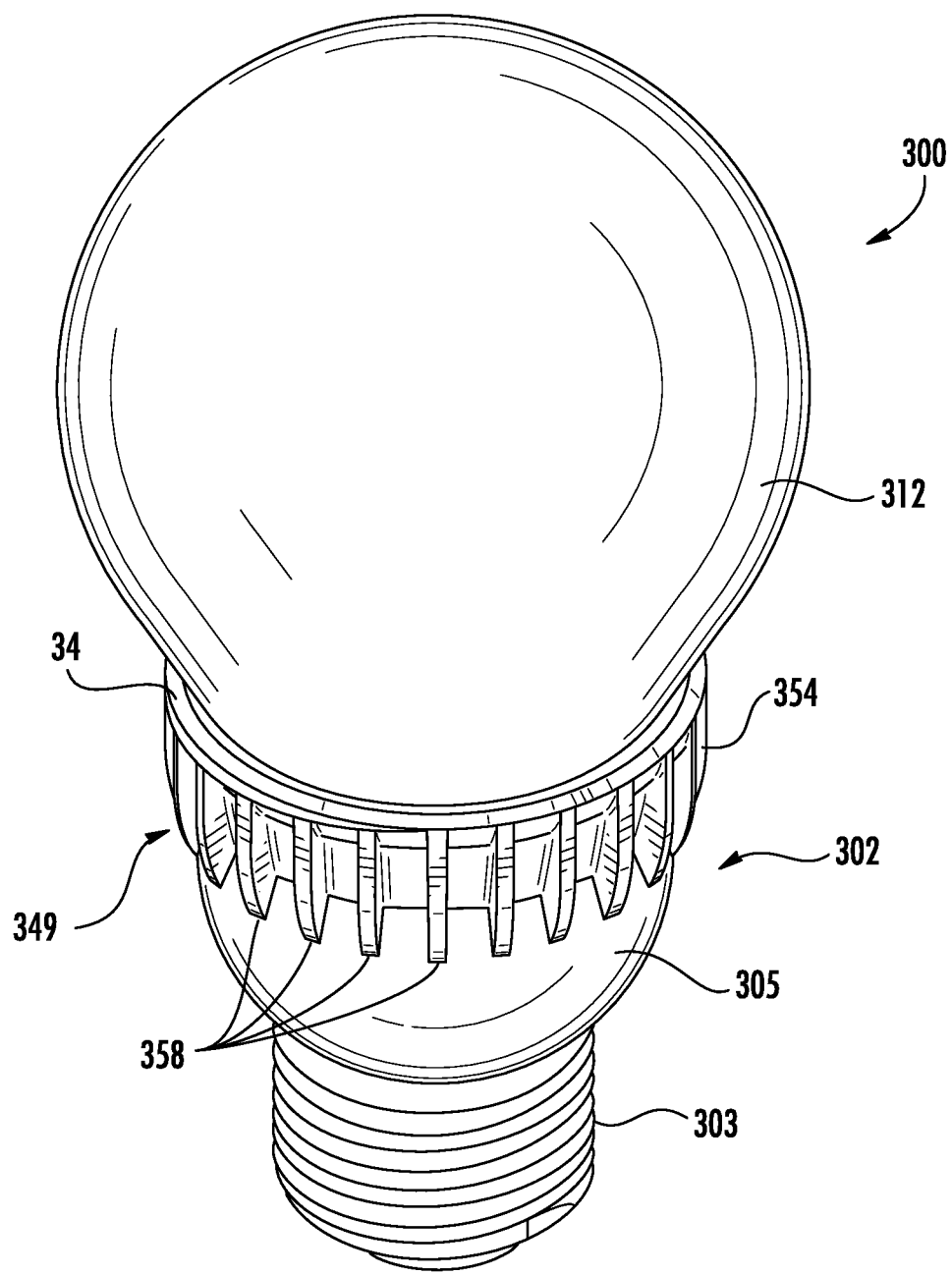
FIG. 5 is a side view of another embodiment of an exemplary LED lamp in which the invention may be used.
Figure 6:
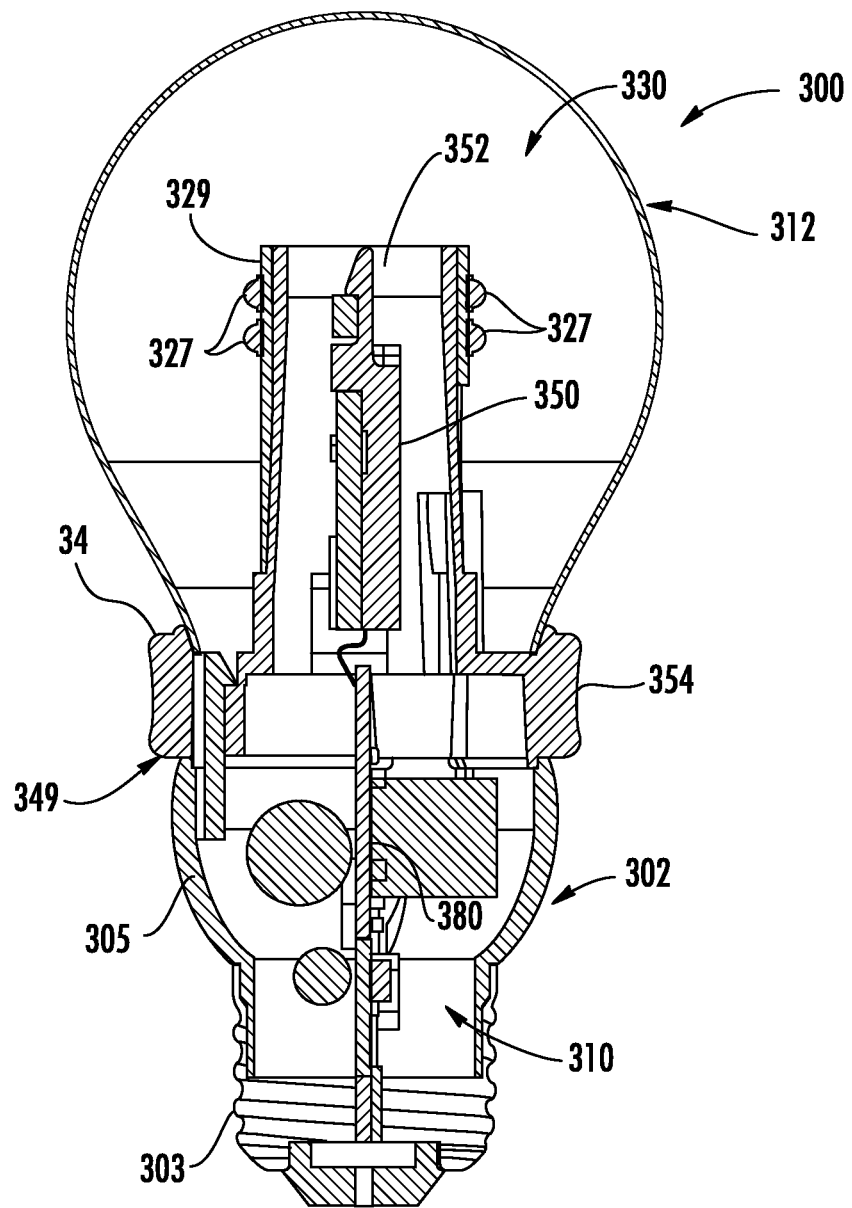
FIG. 6 is a section view of the lamp of FIG. 1.

FIGS. 5 and 6 show another embodiment of a lamp 300 comprising an at least partially optically transmissive enclosure 312 for emitting light from the lamp generated by LEDs 327 located internally of the enclosure. The base 302 comprises an electrical connector 303 in the form of an Edison screw and a housing 305 where the housing does not form part of the heat sink structure 349. The heat sink structure 349 comprises a heat conducting portion 352 that extends into the enclosure 312 in the form of a tower and that supports and is thermally coupled to LED assembly 330 comprising a LED board 329 supporting LEDs 327. The heat conducting portion 352 is thermally coupled to the exposed heat dissipating portion 354 of the heat sink 349. The heat dissipating portion 354 extends to the exterior of the lamp and is positioned between the enclosure 312 and the housing 305. The heat dissipating portion 354 of the heat sink 349 has fins 358 to facilitate dissipating heat to the ambient environment. FIG. 6 also shows the LED electronics 310 for powering the lamp where the LED electronics are mounted on an electronics board 380 that is the electrical path from the connector 303 to the LEDs 327. FIG. 6 also shows an electrical interconnect 350 for electrically coupling the electronics board 380 to the LED board 329.

Figure 7:
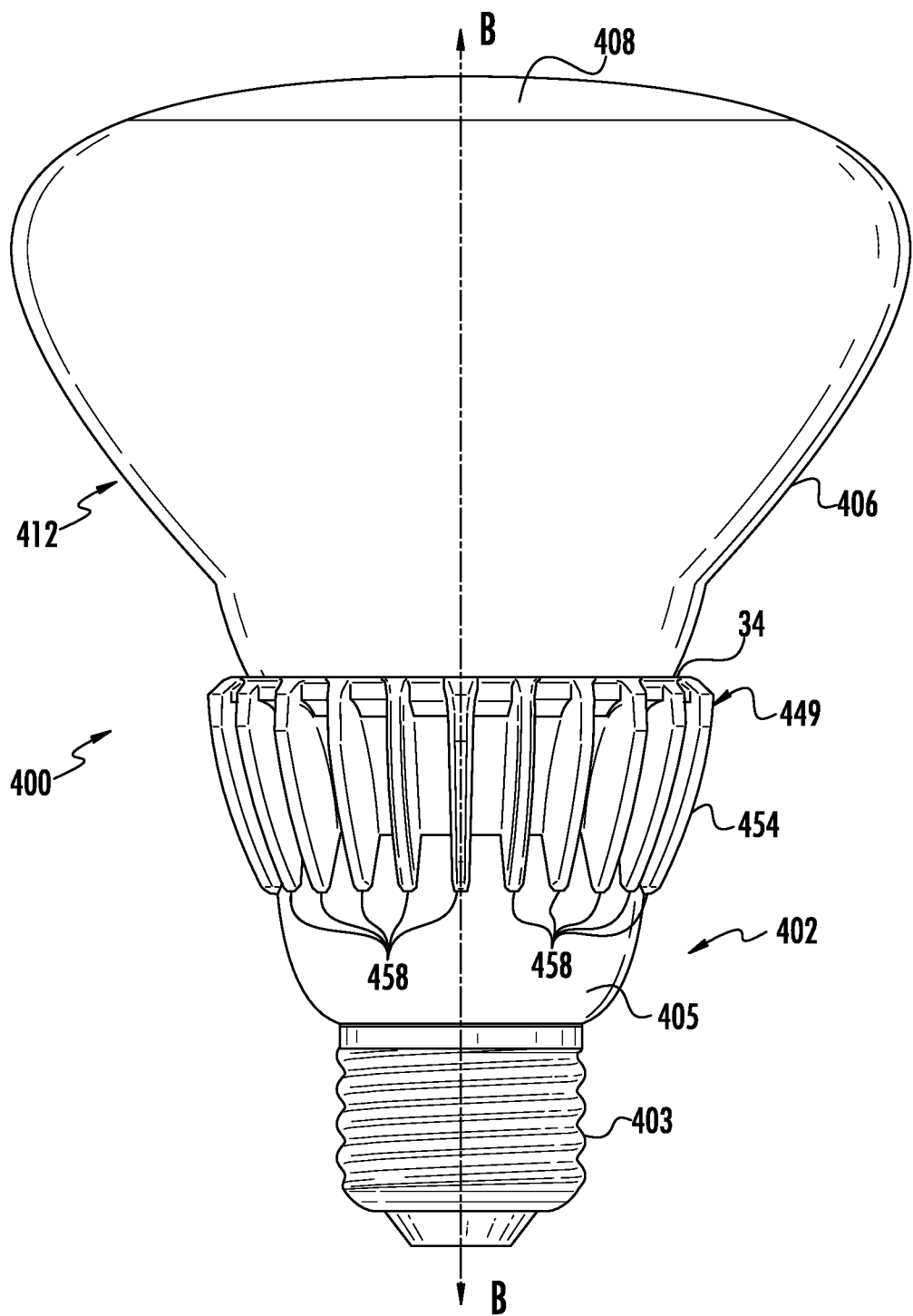
FIG. 7 is a side view of yet another embodiment of an exemplary LED lamp in which the invention may be used.
Figure 8:
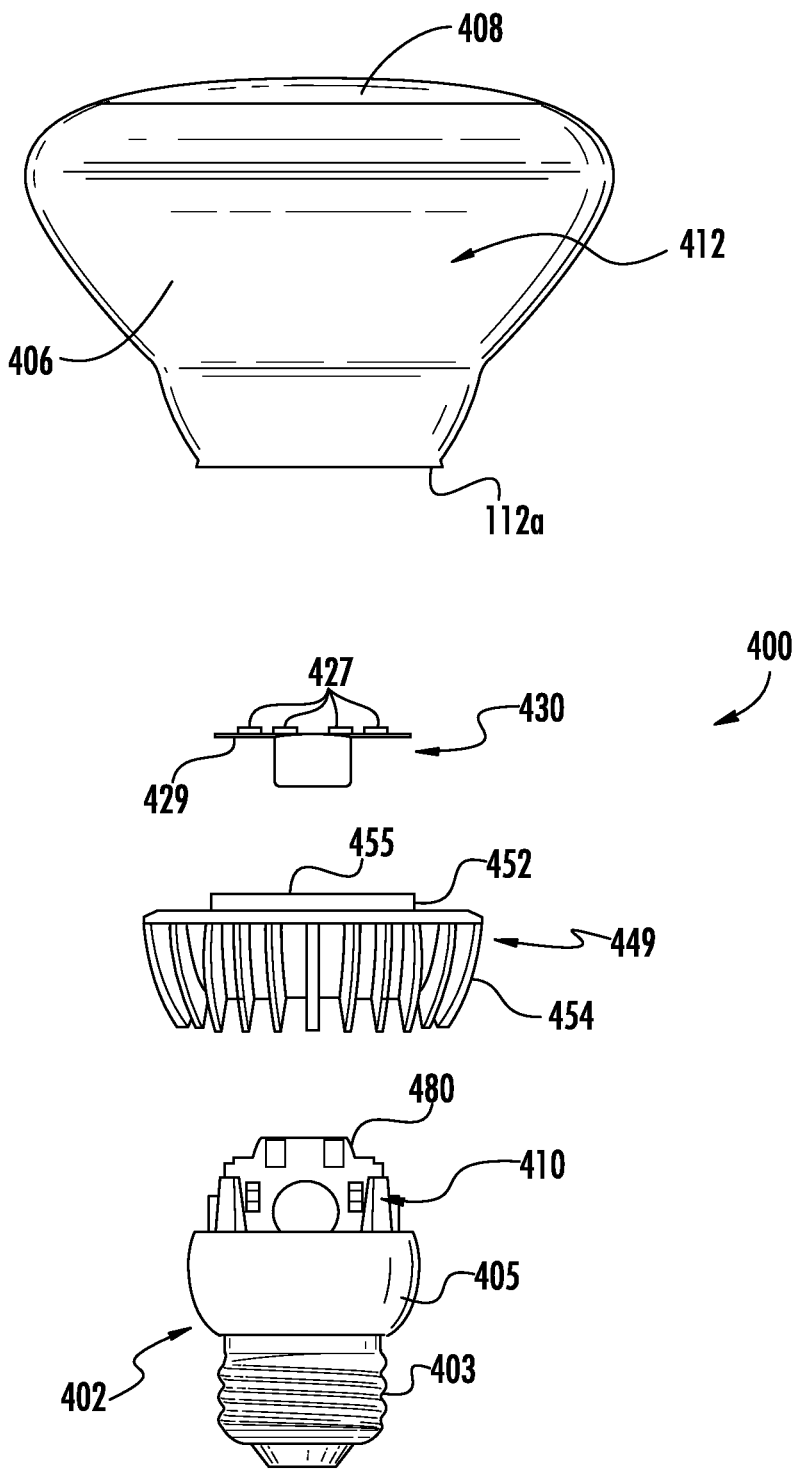
FIG. 8 is an exploded perspective view the lamp of FIG. 7.

The LED lamp of the present disclosure may be configured as a directional lamp such as a PAR-style lamp or a BR-style lamp or flashlight. In a PAR or BR type lamp the light is emitted in a directional pattern. Standard PAR bulbs are reflector bulbs that reflect light in a direction where the beam angle is tightly controlled using a parabolic reflector. PAR lamps may direct the light in a pattern having a tightly controlled beam angle such as, but not limited to, 10°, 25° and 40°. BR lamps have a directional light pattern where the beam angle is generally speaking less tightly controlled than in a PAR lamp. FIGS. 7 and 8 show an example of a directional lamp that has an external configuration similar to the lamp previously described with respect to FIGS. 5 and 6. The base 402 comprises an electrical connector 403 in the form of an Edison screw and a housing 405 where the housing does not form part of the heat sink structure. The heat sink structure 449 comprises a heat conducting portion 452 that extends into the enclosure and that is arranged transversely to the longitudinal axis B-B of the lamp similar to the lamp of FIGS. 1-3 and that supports and is thermally coupled to LED assembly 430 comprising a LED board 429 supporting LEDs 427. The LED board 429 may be mounted on surface 455 of heat sink structure 449. The heat conducting portion 452 is thermally coupled to the heat dissipating portion 454 of the heat sink structure 449. The heat dissipating portion 454 extends to the exterior of the lamp and is positioned between the enclosure 412 and the housing 405. In the embodiment of FIG. 4 the heat dissipating portion 454 of the heat sink has fins 458 to facilitate dissipating heat to the ambient environment. FIG. 8 also shows the LED electronics 410 for powering the lamp where the LED electronics are mounted on an electronics board 480 that is the electrical path from the connector 403 to the LEDs 427. In some embodiments, a reflective surface 406 may reflect some of the light generated by the LED 427. The enclosure 412 may be made of a optically transparent or non-transparent material and an interior surface of the enclosure 412 may be highly reflective such as by polishing the interior surface or by coating the interior surface of housing with aluminum or other highly reflective material. In other embodiments the reflective surface may comprise a separate reflector mounted inside the enclosure. In this and other embodiments the reflectors may be part of the heat sink structure and may be formed a thermally conductive material such as aluminum. The enclosure 412 comprises an optically transmissive exit surface 408 at the top of the enclosure, through which the light exits the lamp. The exit surface may be frosted or otherwise treated with a light diffuser and/or notch filter material Where the lamp is intended to be used as a replacement for a PAR type lamp, the reflector may reflect the light in a tightly controlled beam angle and the reflective surface may comprise a parabolic surface such that light reflecting off of the reflector is emitted from the lamp generally along the axis of the lamp to create a beam with a controlled beam angle. For a BR lamp the reflector may have a variety of configurations. In some embodiments the some or all of the reflector is coated with a light reflective material, or is constructed of a reflective material.

Figure 9:
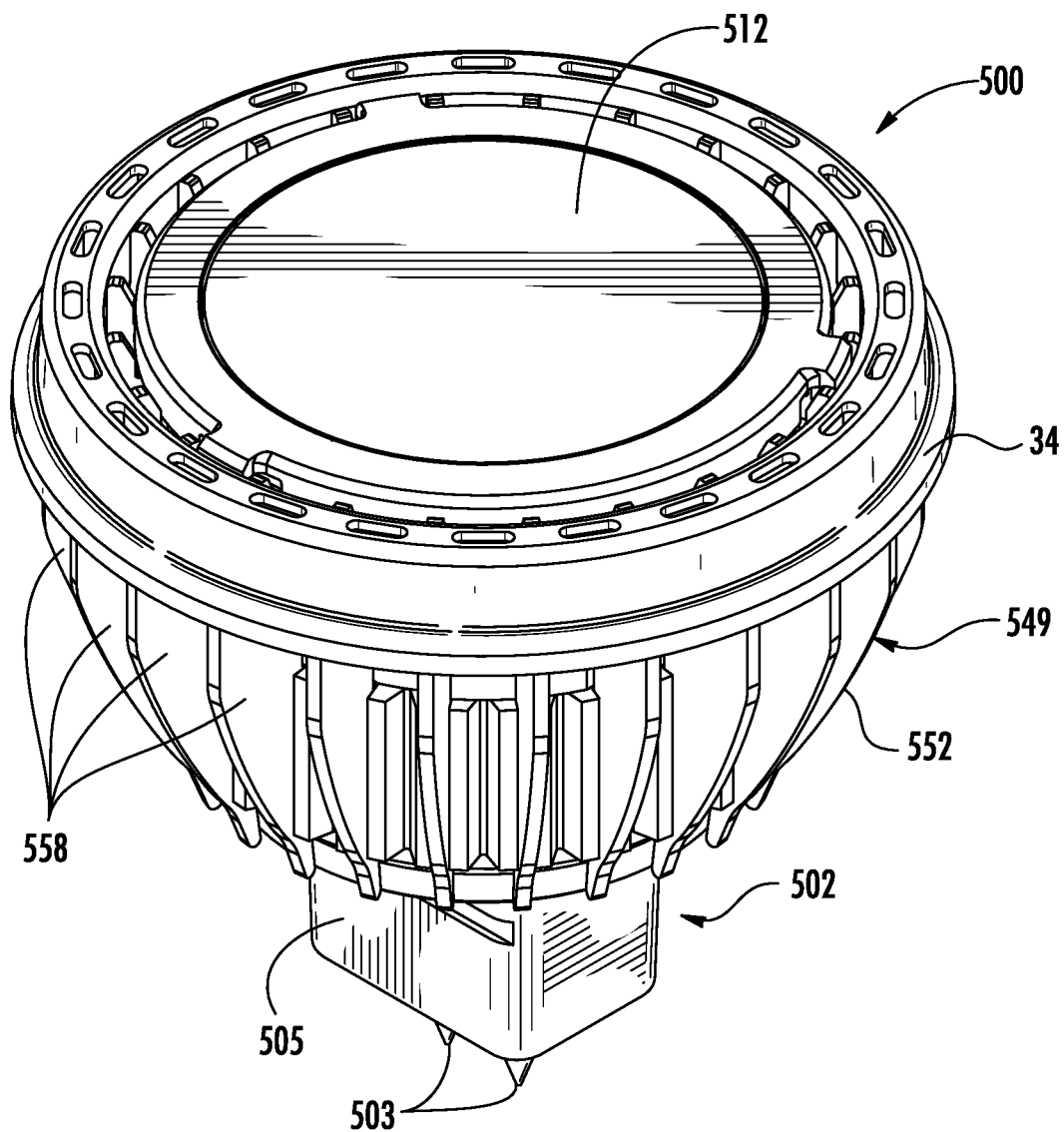
FIG. 9 is a perspective view of still another embodiment of an exemplary LED lamp in which the invention may be used.
Figure 10:
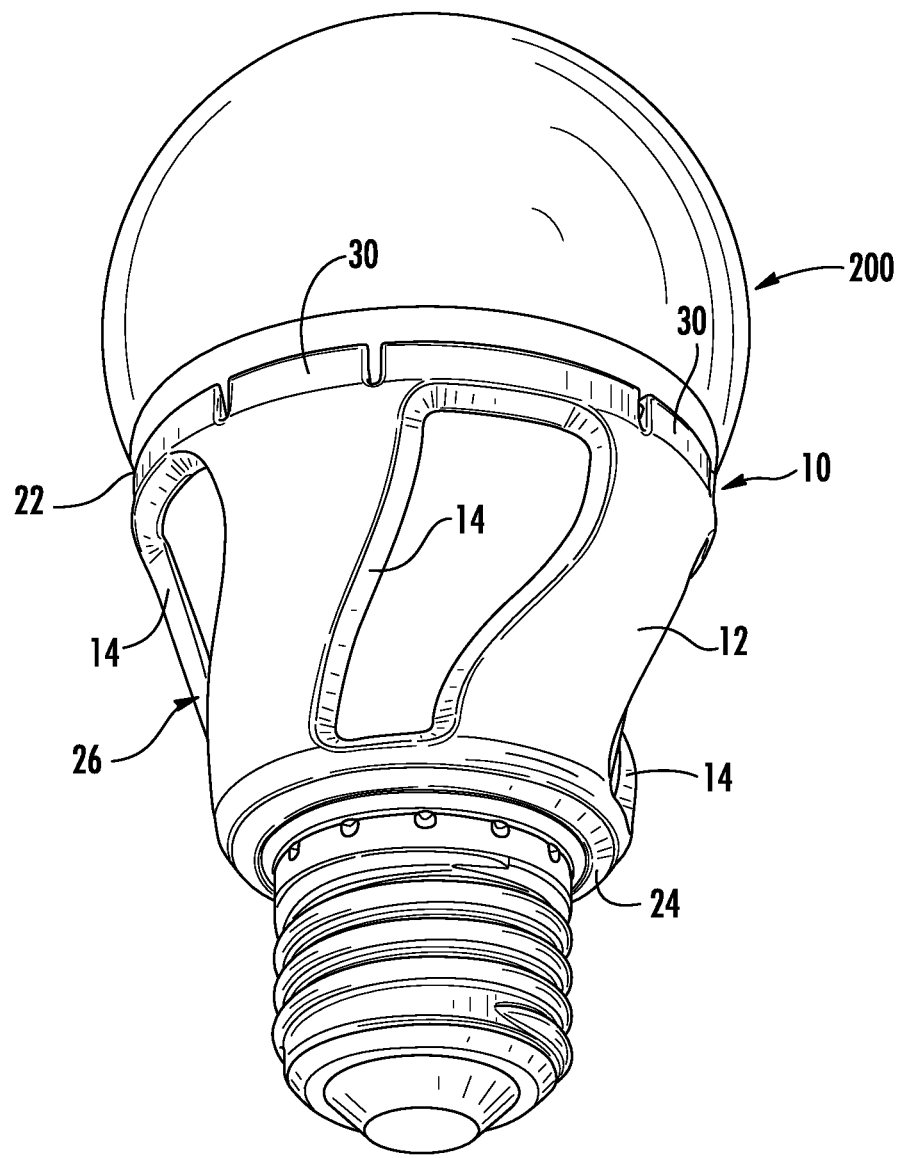
FIGS. 10 and 12 are perspective views of the lamp of FIG. 4 with the aromatic structure of FIG. 4 attached to the lamp.
Figure 12:
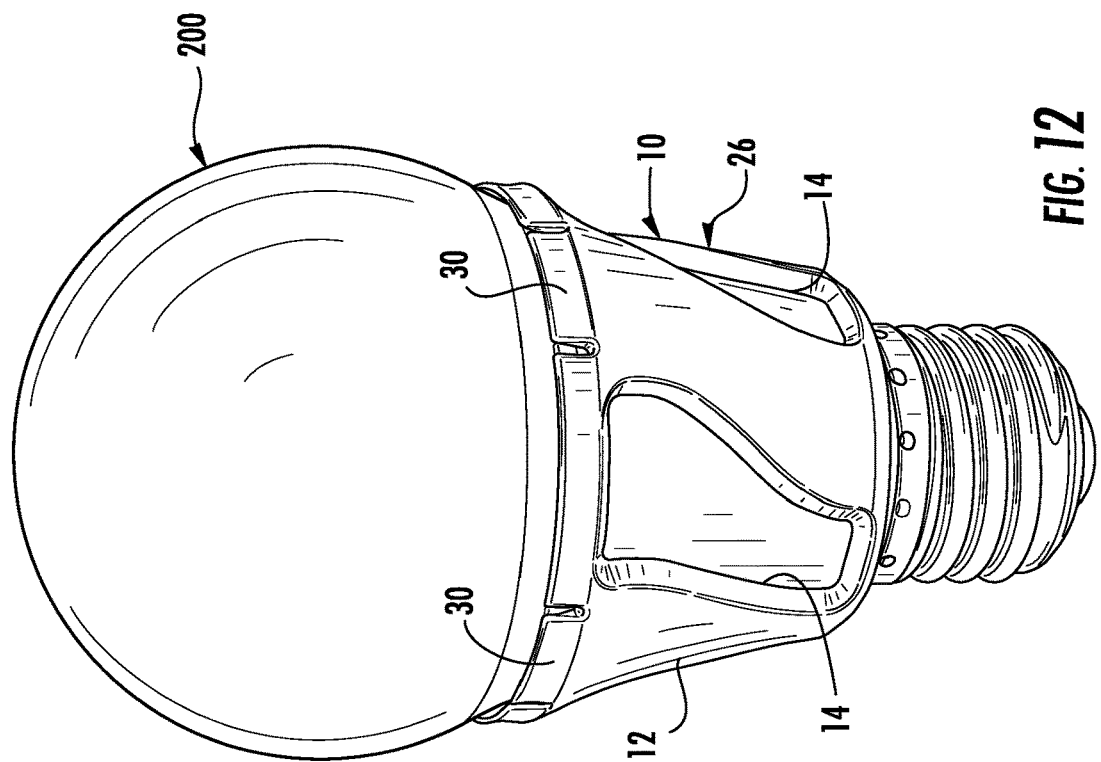

Another embodiment of a lamp 500 is shown in FIG. 9 and may be used as a replacement for a halogen lamp. The lamp includes a base 502 comprising a housing 505 for at least partially retaining the lamp electronics and an electrical connector 503 in the form of a two pin connector. A heat sink structure 549 surrounds the lamp and is thermally coupled to a LED assembly (not shown) that is supported in housing 505. The heat sink comprises a heat dissipating portion 552 comprising heat dissipating members in the form of fins 558. An optically transmissive lens 512 emits light in from the lamp.

In LED lamps electronics boards such as a printed wiring board (PWB), printed circuit board (PCB), lead frame structure, metal core board, metal core printed circuit board, FR4 PCBs, extruded submounts, hybrid combinations of such structures, or other similar structures or combinations of such structures are used to mount components such as the LEDs and lamp electronics. The term "board" as used herein means an electronics board for mounting electronic components ("electronics" as used herein) such as LEDs, drivers, power supplies and/or the like including the types of electronics boards described above where at least a portion of the electrical path to the electrical components is supported on or forms part of the board. In many applications the mounting of such electronic boards may require the mounting and electrical coupling of multiple electronics boards that may be oriented in different planes.

LEDs and/or LED packages used with embodiments of the disclosure can include light emitting diode chips that emit hues of light that, when mixed, are perceived in combination as white light. Phosphors can be used as described to add yet other colors of light by wavelength conversion. For example, blue or violet LEDs can be used in the LED assembly of the lamp and the appropriate phosphor can be in any of the ways mentioned above. LED devices can be used with phosphorized coatings packaged locally with the LEDs or with a phosphor coating the LED die as previously described. For example, blue-shifted yellow (BSY) LED devices, which typically include a local phosphor, can be used with a red phosphor on or in the optically transmissive enclosure or inner envelope to create substantially white light, or combined with red emitting LED devices in the array to create substantially white light.

A lighting system using the combination of BSY and red LED devices referred to above to make substantially white light can be referred to as a BSY plus red or "BSY+R" system. In such a system, the LED devices used include LEDs operable to emit light of two different colors. In one example embodiment, the LED devices include a group of LEDs, wherein each LED, if and when illuminated, emits light having dominant wavelength from 440 to 480 nm. The LED devices include another group of LEDs, wherein each LED, if and when illuminated, emits light having a dominant wavelength from 605 to 630 nm. A phosphor can be used that, when excited, emits light having a dominant wavelength from 560 to 580 nm, so as to form a blue-shifted-yellow light with light from the former LED devices. In another example embodiment, one group of LEDs emits light having a dominant wavelength of from 435 to 490 nm and the other group emits light having a dominant wavelength of from 600 to 640 nm. The phosphor, when excited, emits light having a dominant wavelength of from 540 to 585 nm. A further detailed example of using groups of LEDs emitting light of different wavelengths to produce substantially while light can be found in issued U.S. Pat. No. 7,213,940, which is incorporated herein by reference.

In typical LED lamps the heat generated by the LEDs is simply dissipated to the ambient environment by a heat sink structure such as previously described with respect to FIGS. 1-9. While providing a heat sink that dissipates heat to the ambient environment effectively cools the LED assembly and prevents degradation in the performance of the LEDs, the heat energy is lost. In the lamp of the invention the heat energy generated by the lamp is used in combination with a fragrance infused plastic to generate a pleasant aroma when the lamp is operated. In one embodiment an aromatic structure comprising an aromatic material is thermally coupled to the heat sink structure such that the heat generated by the LEDs that is conducted to the heat sink structure is used to release the aromatics from the aromatic structure. In one embodiment the plastic comprises a cellulose based plastic or polymer material. One suitable material is AURA-CELL™ sold by ROTUBA. The aromatic structure may comprise a plastic material such as a polyolefin, such as polypropylene or polyethylene, EVA, flexible PVC, for example, where the material incorporates with aromatic particles that are released upon heating of the aromatic structure. In a plastic aromatic material the aroma may be released under all ambient conditions; however, the heating of the aromatic structure facilitates the release of the aromatic particles. Heating the aromatic structure facilitate the emission of a scent from the aromatic structure. The aromatic material include homogenous mixing, adsorption onto the surface of an adsorptive material, absorption into the physical structure of an absorbent material, or any other physical or chemical bonding between the aromatic substance that is being incorporated, and the plastic or polymer substance into which it is incorporated.

Figure 11:
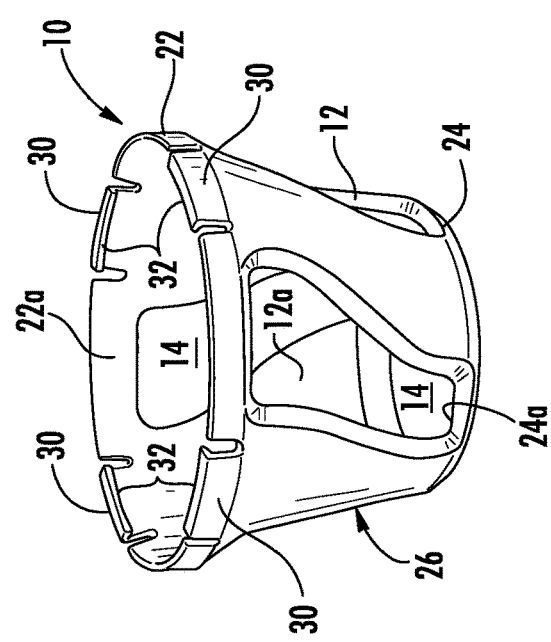
FIG. 11 is a perspective view of the aromatic structure of FIG. 4.
Figure 13:
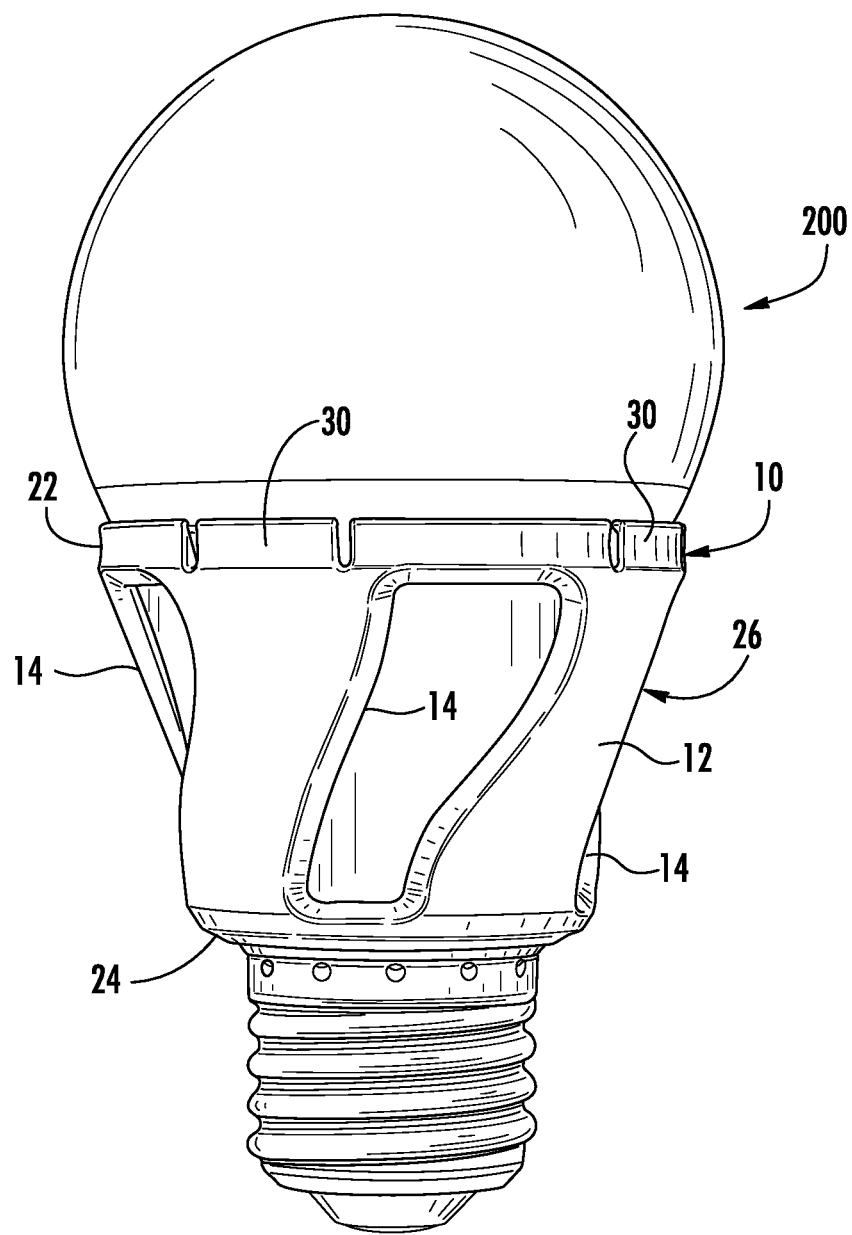
FIG. 13 is a side view of the lamp of FIG. 4 with the aromatic structure of FIG. 4 attached to the lamp.

Referring to FIGS. 4 and 10-14 the aromatic structure 10 may comprise a hollow shell 12 that is separate from the base and heat sink structure of the lamp (see FIG. 11). The aromatic structure 10 may be releasably connected to the lamp such that one aromatic structure may be removed and replaced with another aromatic structure. The aromatic structures may be removed and replaced when the aromatics are depleted and/or to change the aromatics from one type of scent to a different type of scent. For example, different aromatic structures may be infused with different scents such as wintergreen, various fruit scents, spices/herbs, or the like such that the user may select the type of scent and replace one type of scent with another type of scent. While the aromatic structure 10 is shown attached to the lamp 200 as previously described with respect to FIG. 4 the aromatic structure 10 may be mounted to any LED lamp as will be described. The aromatic structure is thermally coupled to the heat sink structure such that heat generated by the heat sink increases the emission of the aromatic substance and the scent associated therewith from the aromatic structure. The aromatic structure may be considered to be thermally coupled to the lamp where heat generated by the lamp increases the emission of the aromatic substance from the aromatic structure. In some embodiments the aromatic structure may be mounted to the lamp but not thermally coupled thereto. The aromatic structure will still emit a scent but at a reduced level when compared to an aromatic structure that is thermally coupled to the heat sink structure.

The shell 12 may openings 14 that allow at least portions of the heat sink structure to be directly exposed to the ambient environment such that the dissipation of the heat from the heat sink to the ambient environment is not impeded by the aromatic structure 10. In one embodiment the aromatic structure 10 comprise an upper end 22 defining aperture 22a configured to circumscribe a larger diameter portion of the heat sink structure and/or base adjacent the enclosure and a narrower lower end 24 defining an aperture 24a configured to circumscribe the narrower diameter portion of the base and/or heat sink structure adjacent the electrical connector. In the illustrated embodiment the shell 12 is round in cross-section to match the form of the lamp base; however, where the lamp has a different shape the shell 12 may have a matching shape. Any suitable shape may be used depending on the configuration of the lamp base. The upper and lower ends 22, 24 are connected by a body 26 that closely matches the shape of the exposed heat sink structure. As previously described the body 26 may include openings 14.

Figure 14:
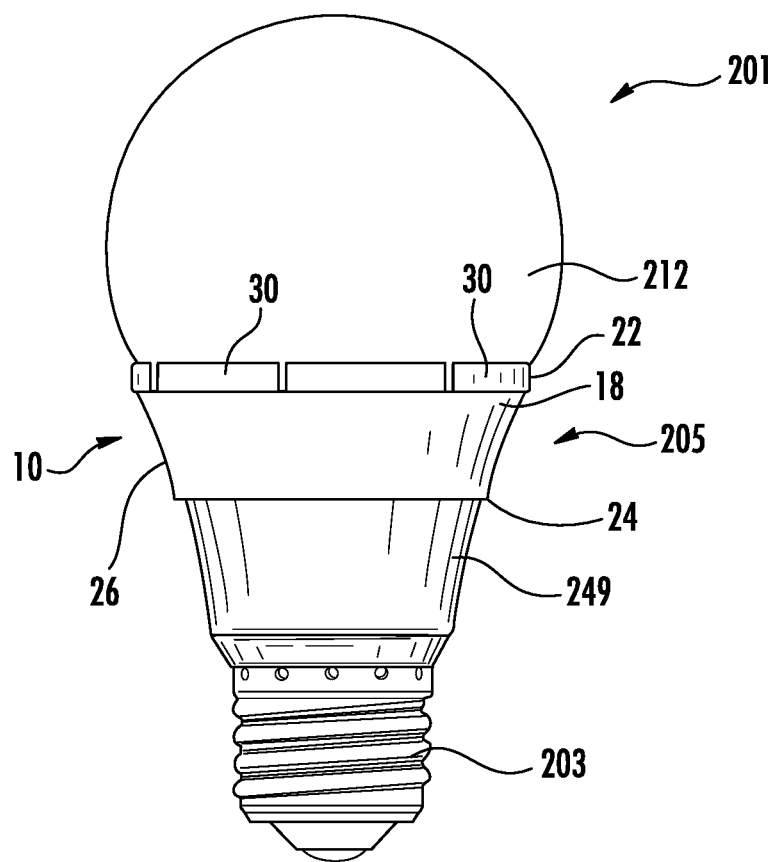
FIG. 14 is a side view of the lamp of FIG. 4 with another embodiment of the aromatic structure of the invention attached to the lamp.
Figure 15:
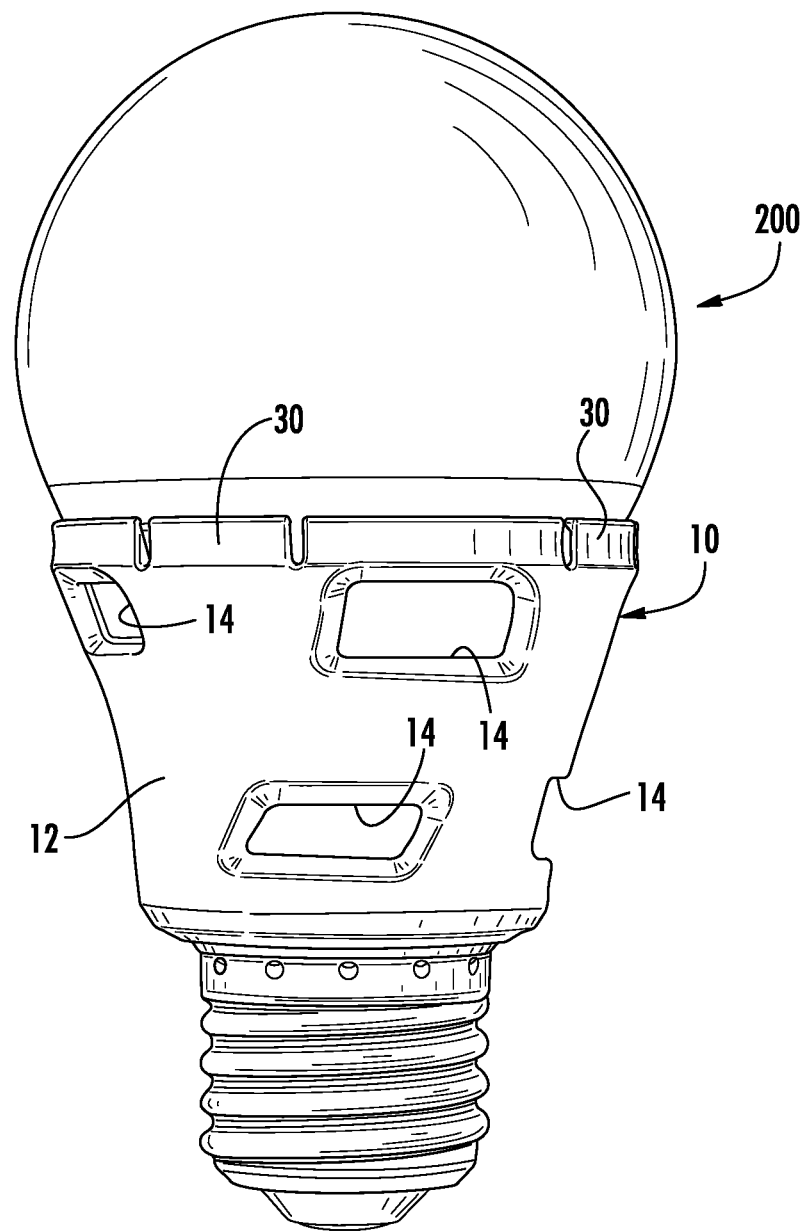
FIG. 15 is a side view of the lamp of FIG. 4 with still another embodiment of the aromatic structure of the invention attached to the lamp.

In other embodiments the aromatic structure 10 may be formed as a solid ring 18 that surrounds the heat sink and does not include openings as shown in FIG. 14. The ring 18 may extend for less of the height of the exposed heat sink structure 249 (along the longitudinal axis of the lamp) such that at least a portion of the heat sink structure 249 is directly exposed to the ambient environment such that the dissipation of the heat from the heat sink to the ambient environment is not impeded by the aromatic structure 10. In other embodiments the shell 12 and apertures 14 may have other shapes as exemplified in FIG. 15.

The configuration and dimensions of the interior surface 12a aromatic structure 10 may be designed to closely match the external dimensions and configuration of the heat sink structure and/or base such that the aromatic structure 10 contacts the heat sink structure over a substantial portion of interior surface 12a as shown for example in FIGS. 4 and 10-15. In such embodiments, the aromatic structure may be design to specifically mate with a particular lamp geometry such that a close fit is established between the heat sink and the aromatic structure. In other embodiments, the aromatic structure may be designed to fit over the heat sink but not necessarily closely mate with the heat sink. In such an embodiment the aromatic structure may be design to fit over the envelope of a standard lamp. For example the aromatic structure may be designed to fit over the envelope of an A19 lamp but the aromatic structure may not have a tailored fit to a particular lamp geometry. In such an embodiment the aromatic structure may be closely adjacent to the heat sink structure but it may not be in contact with the heat sink structure over its entire surface. The heat from the heat sink will heat the aromatic structure to release the aromatics even without direct surface to surface contact between the heat sink structure and the aromatic structure over its entire surface.

To connect the aromatic structure 10 to the lamp a variety of connection mechanism may be used. Because in most lamp configurations the lamp base tapers from a narrow portion adjacent the electrical connector to a wider portion adjacent the enclosure. In some embodiments the shell 12 is slid onto the lamp in the direction of arrow A (FIG. 4). The tapered aromatic structure 10 once mounted on the lamp is prevented from moving toward the enclosure due to the mating tapered geometries of the lamp and shell; therefore, the connection mechanism may be configured to prevent the aromatic structure from moving toward the electrical connector and sliding off the end of the lamp in a direction opposite to arrow A. In one embodiment, as shown in FIGS. 4 and 10-15 a snap-fit connection may be used to connect the aromatic structure and the lamp. For example the aromatic structure may include engagement members 30 such as resiliently deformable tabs that are positioned to engage a mating structure on the lamp. For example, the resilient tabs 30 may comprise extending flanges 32 that engage in a snap-fit manner an edge surface 34 of the base and/or heat sink such that the aromatic structure 10 is clamped to the lamp by the engagement members. The aromatic structure is prevented from moving in a first direction (arrow A) by the geometry of the lamp and is prevented in moving in the opposite direction by the engagement members. While the design of LED lamps may vary from lamp model to lamp model, most LED lamps have edge surfaces created either within a component or where various components of the lamp meet. With lamps having the tapered geometry described above, any surface that faces away from the base may be used as the edge surface 34. The engagement members 30 may be located at any position on the aromatic structure such that the engagement members can engage the edge surfaces.

Figure 16:
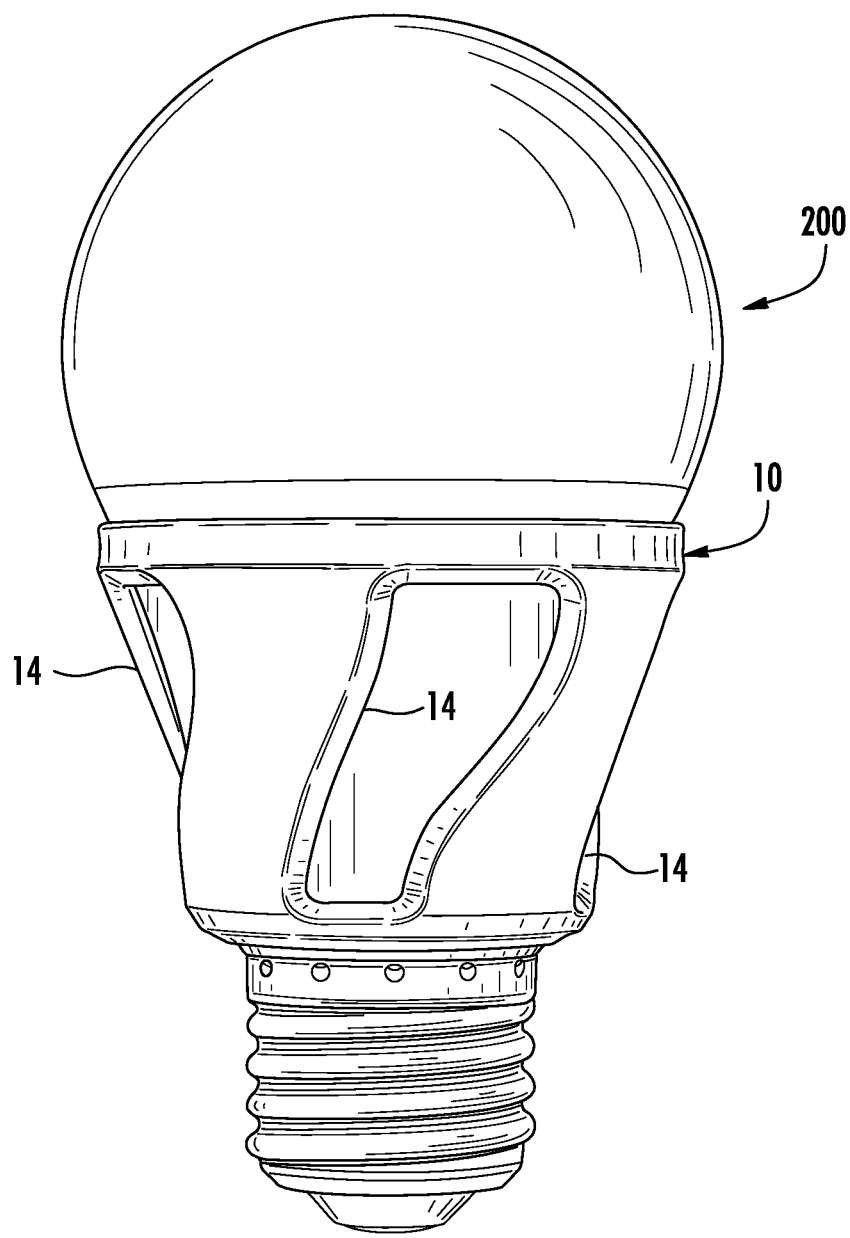
FIG. 16 is a side view of the lamp of FIG. 4 with yet another embodiment of the aromatic structure of the invention attached to the lamp.

In other embodiments, where the aromatic structure is configured to closely fit a particular lamp base and heat sink, the aromatic structure may be attached using a friction fit where the tapered aromatic structure is simply forced into tight engagement with the tapered base and the deformable resilient tabs 30 are not used as shown in FIG. 16. The aromatic structure may be resiliently deformable such that a tight fit may be created between the heat sink structure and the aromatic structure.

Figure 17:
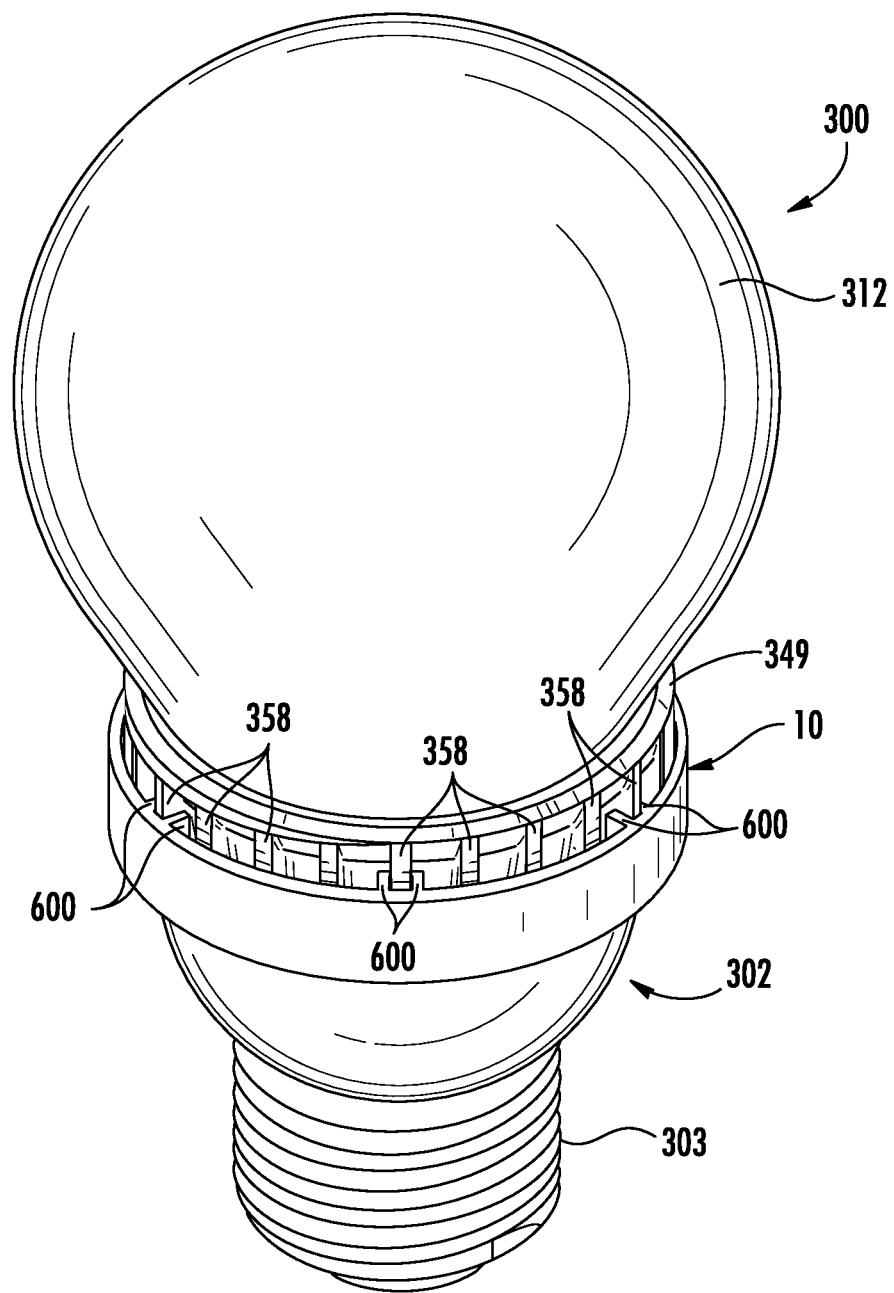
FIG. 17 is a side view of the lamp of FIG. 5 with yet another embodiment of the aromatic structure of the invention attached to the lamp.

The aromatic structure may comprise snap-fit or friction fit members that engage any suitable portion of the base and/or heat sink structure. For example, the engagement structure may engage the fins, edges of the base or heat sink or other lamp structure. As shown in FIG. 17 the aromatic structure 10 may include closely spaced flanges 600 that face the heat sink 349 and grip heat sink fins 358 therebetween. The flanges 600 may be resiliently deformable such that the flanges may be deformed and separated to grasp a fin such that the resilient material creates a holding force sufficient to hold the aromatic structure 10 on the heat sink structure. The flanges 600 may engage some or all of the fins as sufficient to hold the aromatic structure to the heat sink structure 349. In other embodiments the aromatic structure 10 may include spaced, opposed deformable tabs 700, 702 that face the heat sink structure and grip opposite ends of the exposed portion of the heat sink structure to clamp the heat sink structure therebetween as shown in FIG. 18. While in some embodiments the aromatic structure 10 is shown completely encircling the heat sink, the aromatic structure may extend for less than the full circumference of the heat sink structure as shown in FIG. 19. In such an embodiment, the aromatic structure 10 may have a C-shape and may be deformed to allow the heat sink 149 to be inserted into the aromatic structure through the gap 710 or the aromatic structure 10 may be slipped over the end of the heat sink 149 and secured thereto as described herein.

Figure 20:
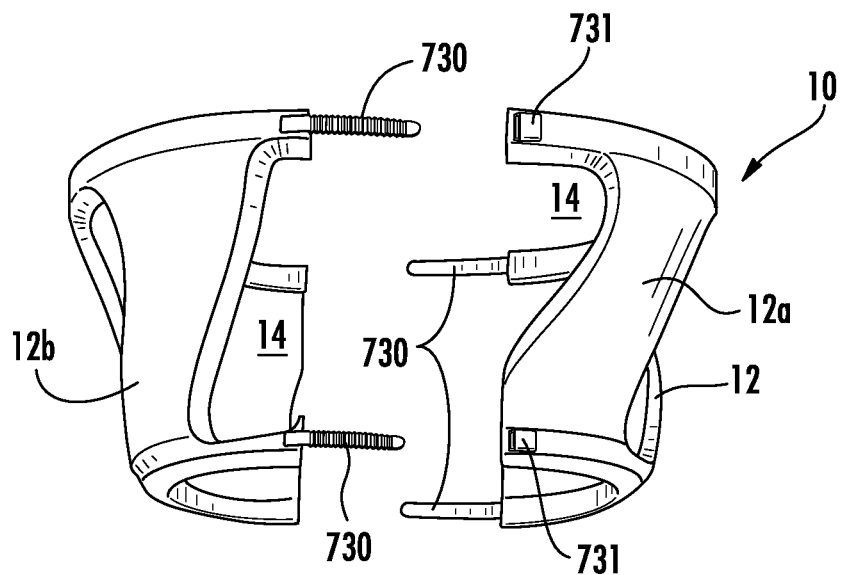
Figure 21:
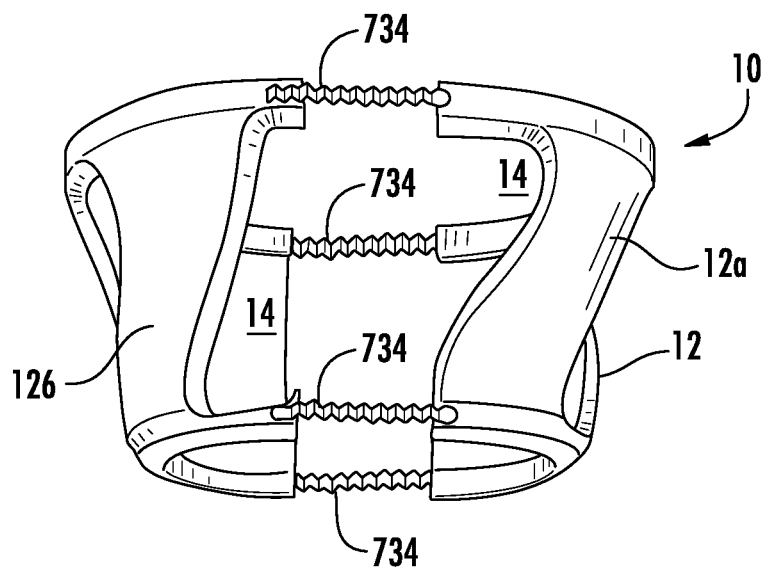

In embodiments where the aromatic structure does not closely receive the base, such as where the aromatic structure is designed to engage a class of lamp such as an A19 lamp but is not designed to engage a specific manufacturer's model, the engagement structure may comprise an adjustable engagement mechanism. For example, as shown in FIG. 20, the engagement structure may comprise straps 730 that may be used to tighten the aromatic structure on the heat sink. In some embodiments the shell 12 may be formed as separate parts 12a, 12b that surround the exposed heat sink as shown in FIG. 20 and are connected to one another by adjustable straps 730 to trap the heat sink therebetween. The straps 730 may comprise zip ties or other self-tightening and self-locking members. The straps 730 may be connected to one of the portions 12a, 12b that adjustably connect to mating locking mechanisms 731 on the other one of the two portions 12a, 12b. The straps may also be used to pull portions 10a, 10b of the shell 12 into close engagement with the base and heat sink structure. The straps may also comprise elastic bands 734 that pull the portions 12a, 12b of the aromatic structure 10 into engagement with the heat sink structure as shown in FIG. 21. The straps may be formed as resilient accordion style bands that are made as one piece with the plastic portions 12a, 12b. In other embodiments the engagement structure may comprise set screws 740 (FIG. 22), adhesive, adhesive pads 742 (FIG. 23) or the like. Referring to FIG. 24, in other embodiments the shell 12 may be formed as a single part where portions 12a, 12b of the part may be tightened or attached to the base using one of the attachment mechanisms discussed above. The portions 10a, 10b of the shell 12 may rotate relative to one another at a hinge such as living hinge 750 and use a connector such as straps, elastic bands or the like to pull the aromatic structure into tight engagement with the heat sink structure.

Figure 25:
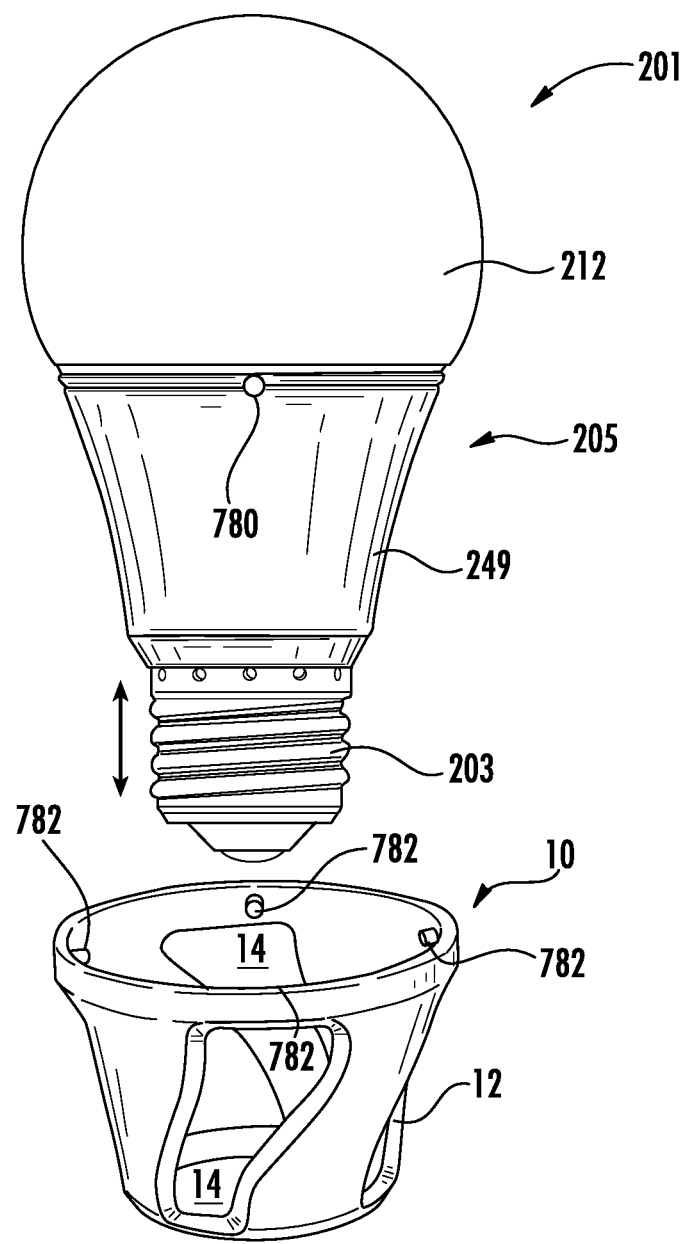
FIG. 25 is a perspective view of another embodiment of the aromatic structure of the invention removed from a lamp similar to the lamp of FIG. 4.

Referring to FIG. 25, in other embodiments the base and/or heat sink 249 may be formed with engagement members 780 that engage mating engagement members 782 on the shell 12. For example one of the base and/or aromatic structure may be provided with male members 782 that engage female receptacles 780 formed on the other one of the base and/or aromatic structure using a snap-fit, pressure fit, friction fit or the like.

The removable aromatic structures described herein are removable and replaceable such that the aromatic structures may be manufactured, marketed and sold separately from the lamp. The user may select the type of aromatic structure and connection mechanism suitable for the lamp and may select aromatic structures having a wide variety of scents. As described above the aromatic structures may be made to be specifically compatible with certain makes and models of lamps or the aromatic structures may be made compatible with a range of lamps using a universal connection mechanism.

In other embodiments, the aromatic structure may be permanently formed as part of the lamp such that the aromatic structure is not removable from the lamp. As previously described, the aromatic structure may be made of a moldable plastic such that the aromatic structure may be molded over the base and heat sink such that the aromatic structure is in close conformity with the heat sink structure. The aromatic structure may be formed over the heat sink structure using any suitable manufacturing method such as insert molding, overmolding or the like. In such an embodiment the aromatic structure would be permanently attached to the base and/or heat sink structure and would not use one of the removable connection mechanisms described above. The lamp with the permanently attached aromatic structure would have a visual appearance similar to the embodiment shown in FIG. 16 where no releasable connection mechanism is used but where the aromatic structure 10 is permanently attached to the lamp.

In other embodiments, the aromatic structure may be formed as part of the lamp structure rather than as a separate aromatic structure secured to the heat sink structure. Referring to FIGS. 5, 7 and 9 for example, the aromatic structure could be molded to form housing 305, housing 405 or housing 505 such that the aromatic structure forms an integral component of the lamp rather than being a separate component secured to the lamp. As shown in FIGS. 5, 7 and 9 the housings 305, 405, 505 are in contact with the heat sinks 354, 454, 549 respectively, such that the aromatic material of the housings 305, 405, 505 is heated by heat from the heat sinks 354, 454, 549 respectively, to foster the emission of the aromatics. As previously described, in some embodiments the heat sink structure itself or portions of the heat sink structure may be made of thermal plastic such that the plastic heat sink forms part of heat sink structure of the lamp. The thermal plastic used to form the heat sink structure may be infused with an aromatic such that the aromatic structure and the heat sink structure or portions of the heat sink are the same structure. The heating of the heat sink to dissipate heat from the lamp will also disperse the aromatics from the plastic.

Figure 26:
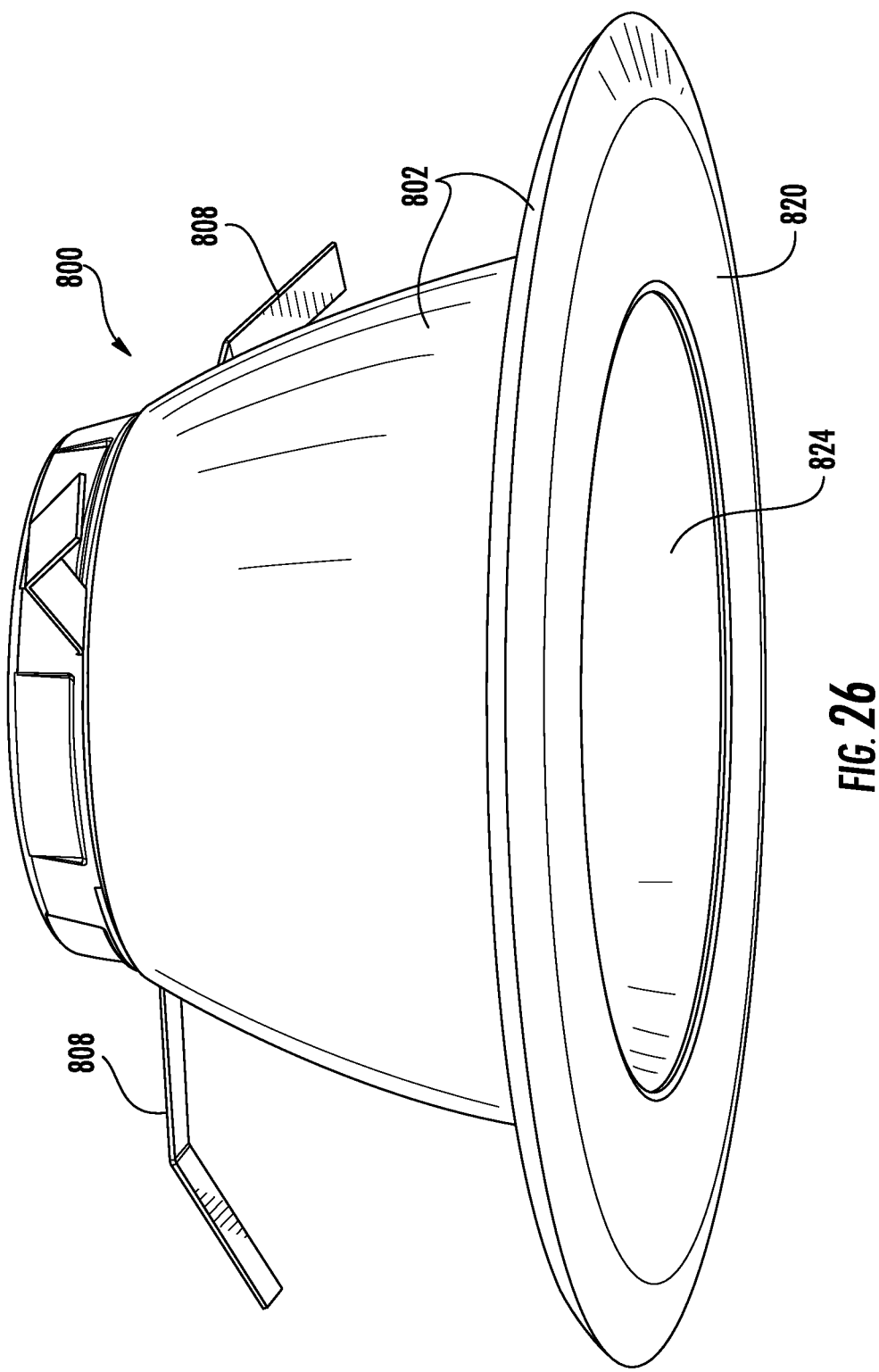
FIG. 26 is a perspective view of an embodiment of an exemplary LED lamp including an embodiment of the aromatic structure of the invention.
Figure 27:
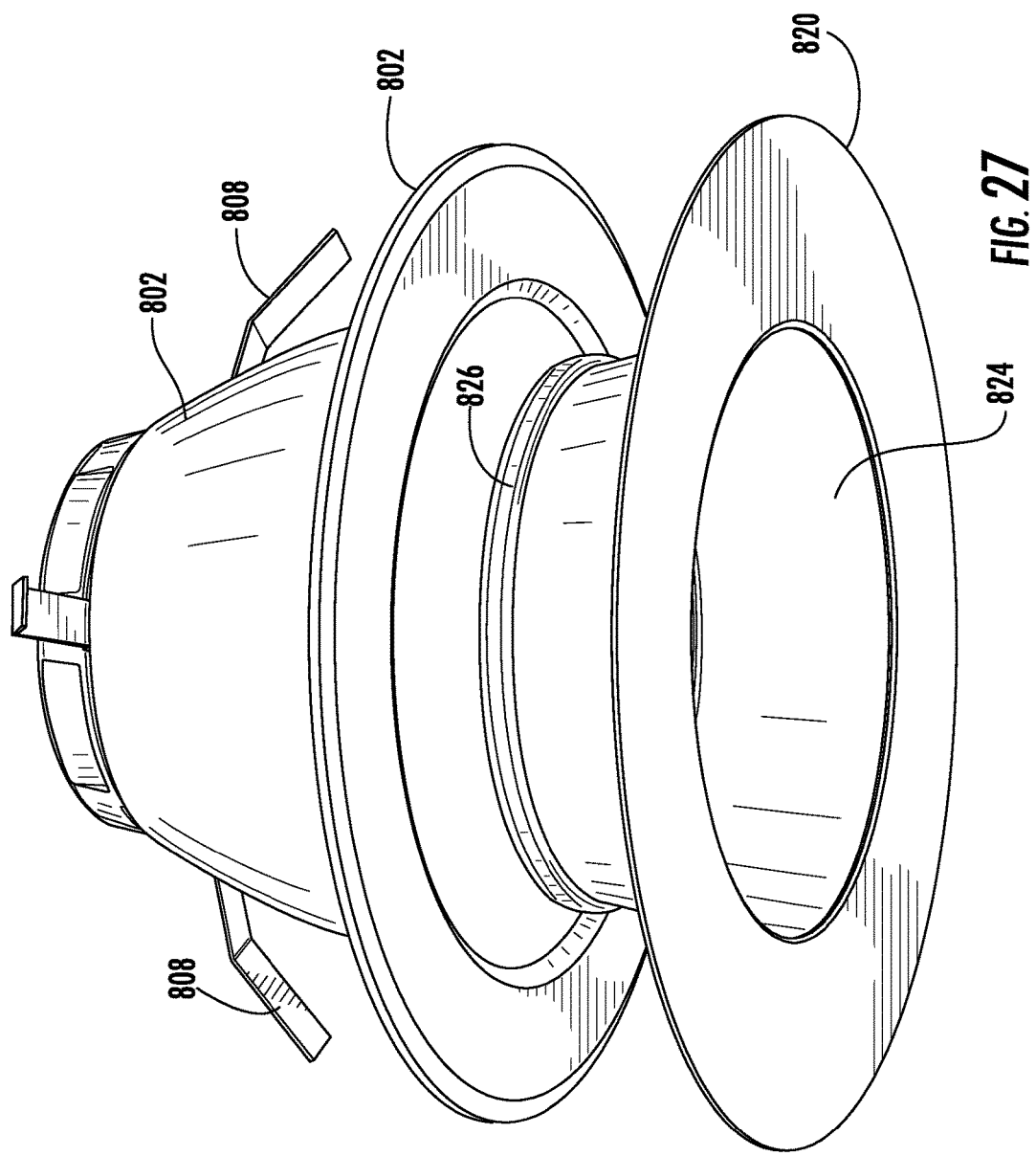
FIG. 27 is an exploded perspective view of the lamp and aromatic structure of FIG. 26.
Figure 28:
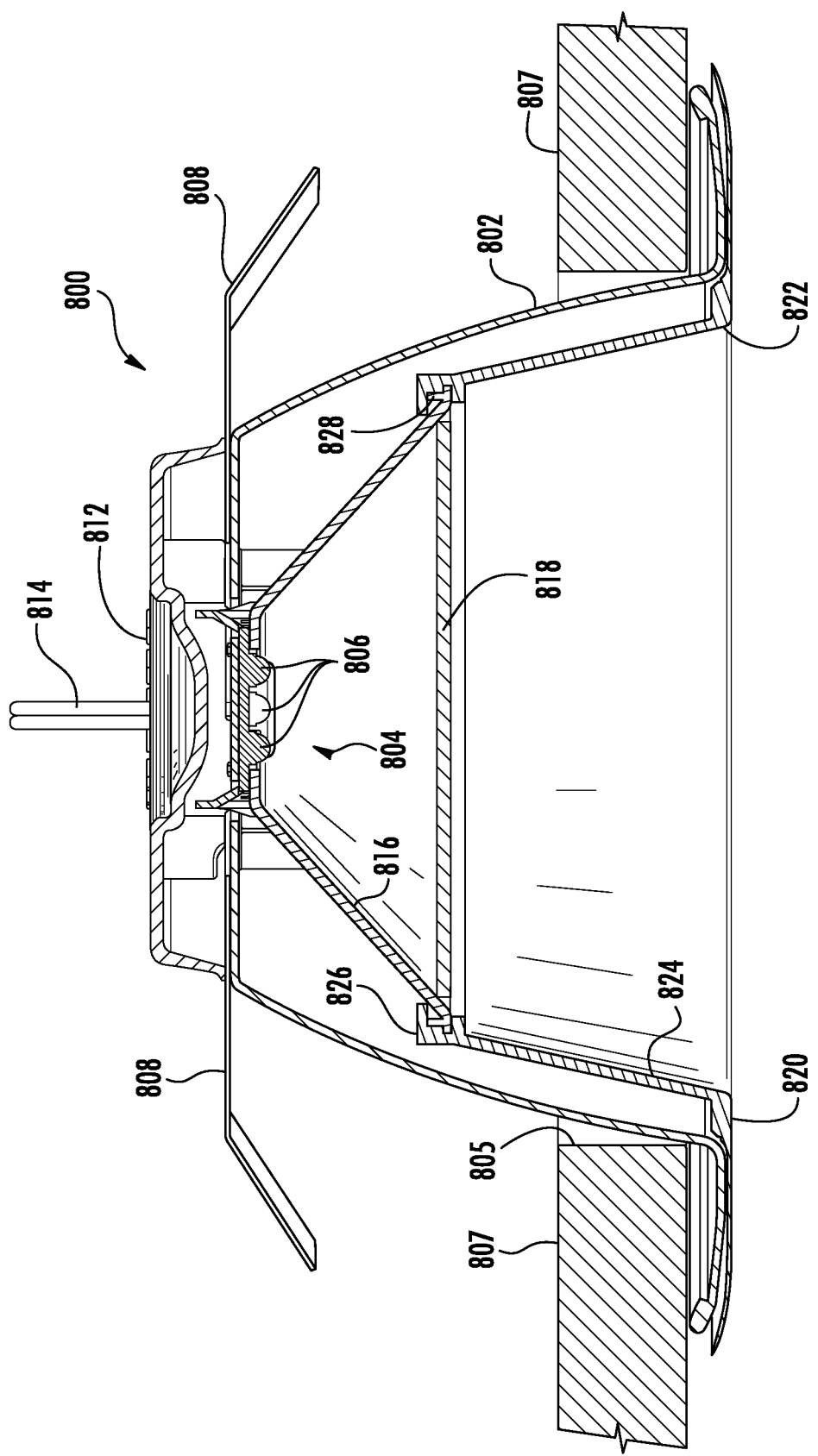
FIG. 28 is a section view of the lamp and aromatic structure of FIG. 26.
Figure 29:
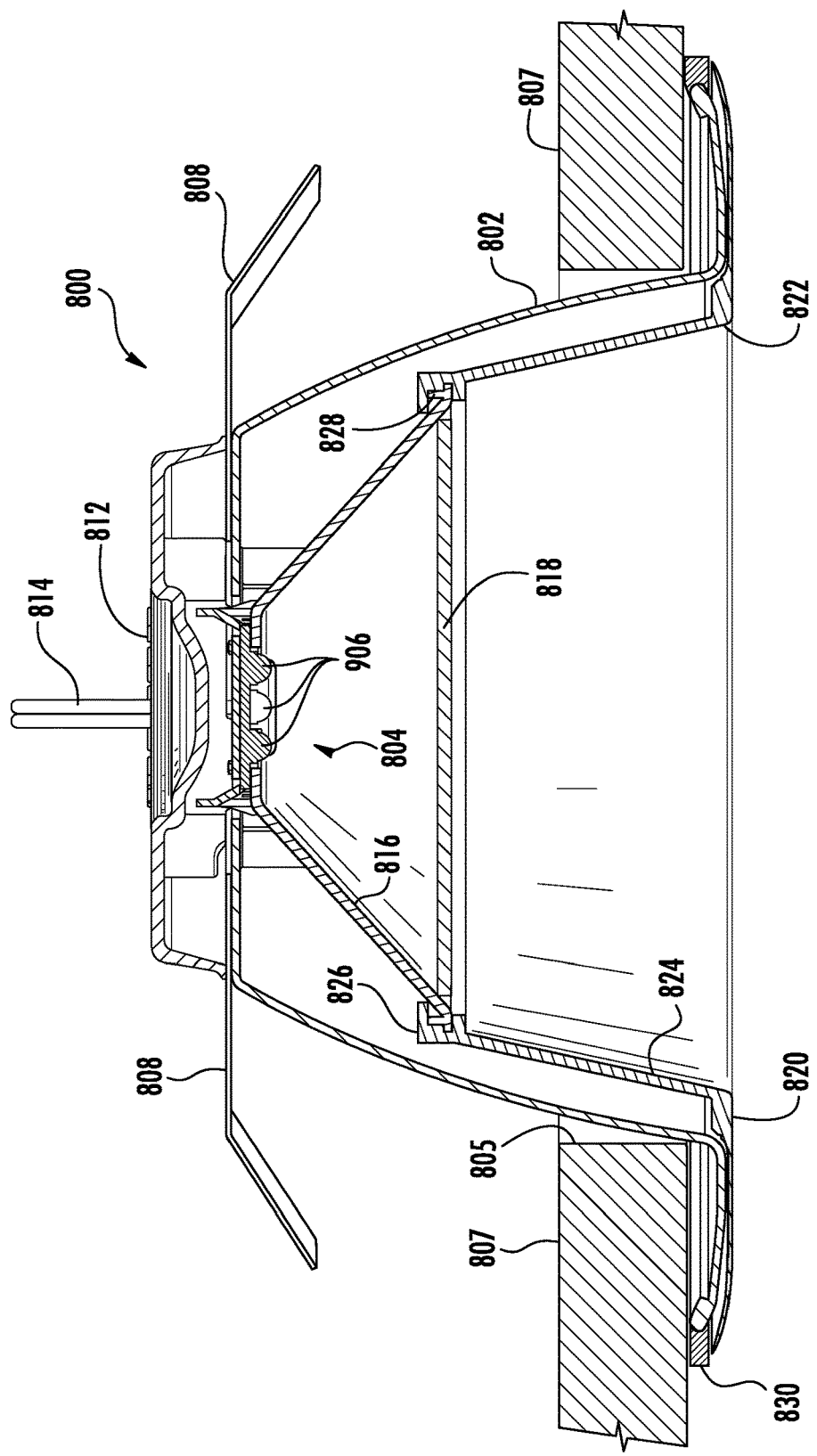
FIG. 29 is a section view of an embodiment of an exemplary LED lamp in which the invention may be used and an embodiment of the aromatic structure of the invention mounted to the lamp.

Referring to FIGS. 26-28, in other embodiments the aromatic structure may be used with directional lamps such as downlights or "can" lights. Such lamps are typically located in a hole formed in a ceiling or other structure and are recessed into the ceiling such that the bottom edge of the lamp is substantially flush with the ceiling. Such lamps may take a variety of forms including new LED light fixtures and retrofit LED fixtures. In a new LED light fixture the entire legacy light fixture is replaced by a complete LED light fixture while in a retrofit LED light fixture at least some of the electronics and/or physical structure of the legacy fixture is retained. While such fixtures may take many forms they typically include common elements. FIGS. 26-28 show an example LED downlight 800 comprising a housing 802 for retaining the LED assembly 804. The LED assembly 804 comprises at least one and typically a plurality of LEDs 806. The lamp electronics 812 for powering and controlling operation of the LEDs 806 may form part of the LED assembly and/or be supported in or on the housing 802, or the lamp electronics may be supported spaced from the housing and be electrically coupled to the LEDs. Suitable electrical conductors 814 such as wiring or the like connect the LEDs to the lamp electronics and/or a power source. The housing 802 is typically positioned in an aperture 805 formed in the ceiling 807 or other structure such that the light is emitted into the room generally downward; however, other orientations of the light fixture are possible. The LEDs 806 are typically thermally coupled to the housing 802 and the housing 802 is made of a thermally conductive material such that heat generated by the LEDs may be transferred away from the LEDs and dissipated to the ambient environment by the housing. A mounting structure 808 for mounting the light fixture to the ceiling or the ceiling support structure such as joists may also be provided. Further these lamps also typically comprise optical elements for color mixing, shaping and directing the light emitted from the lamp. The optical elements may include a reflector 816, lens 818 and/or other optical elements. The reflector 816 may be thermally coupled to the LEDs and may be made of a thermally conductive material and form part of the heat sink structure. It is common in such light fixtures that a decorative trim ring 820 is used to provide a clean look for the finished lamp. Because the housing may not be made to be aesthetically pleasing and the interface between the housing and the aperture 805 may be rough, the trim ring 820 is placed over the housing and the housing/ceiling interface to create a clean aesthetically pleasing appearance. The trim ring 820 typically comprises an annular shaped ring that covers the housing and the housing/ceiling interface. Light is emitted through the central opening 822 of the trim ring 820. The trim ring 820 may also include optical elements for shaping or treating the light. For example the trim ring 820 may have a reflector surface 824, lens (not shown) or the like. Because the trim ring 820 is used as a decorative part it is typically installed to the housing separately after the light fixture is installed in the lamp. In a typical light fixture the trim ring 820 is removable and replaceable such that different style, color etc. trim rings may be used with the same light fixture. Because the trim ring 820 is removable in a typical light fixture the trim ring and light fixture have a mounting structure that allows the trim ring to be mounted on and removed from the remainder of the light fixture even after the light fixture is installed. In the embodiment of FIG. 26-28 the trim ring includes an annular flange 826 that removably receives the mating rim 828 of reflector 816.

The trim ring 820 comprises the aromatic structure as previously described where the trim ring 820 comprises a plastic material infused with an aromatic substance. Because the trim ring contacts or is in close proximity to the heat conducting portions of the light fixture such as housing 802 and reflector 816 the heat generated by the lamp heats the aromatic structure to facilitate release of the scent. While in one embodiment the aromatic structure comprises the trim ring, the aromatic structure may also be another component of the light fixture. For example the reflector 816 may be the aromatic structure. In other embodiments a separate component that is mounted to the heat sink structure may comprise the aromatic structure. For example an aromatic structure 830 may be separately mounted to or in the housing or on the heat sink structure. In the illustrated embodiment the aromatic structure may comprise a ring that fits over the exposed end of the housing; however, the aromatic structure 830 may have other shapes and be mounted on other areas of the heat sink structure of the light fixture.

Figure 30:
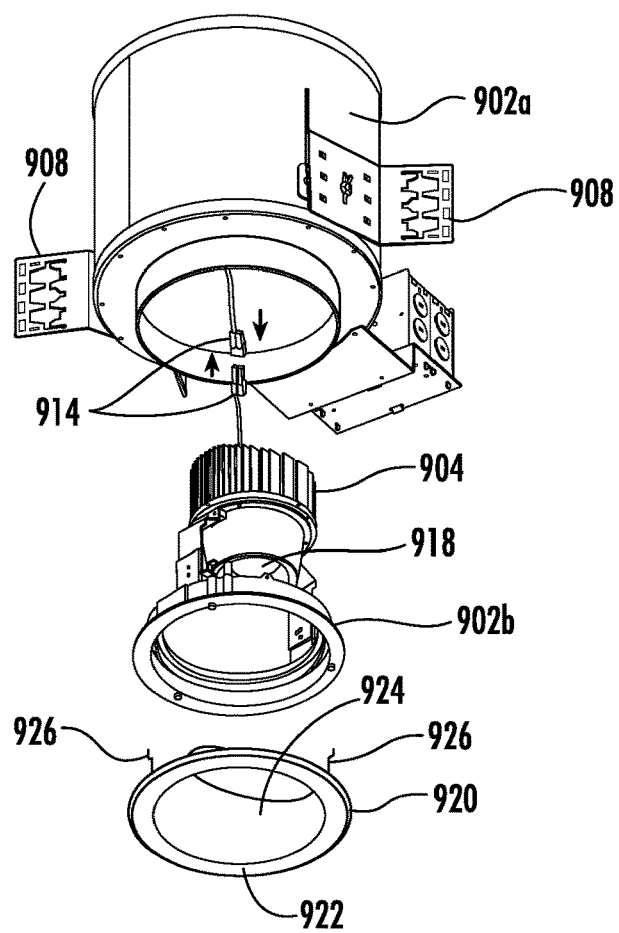
FIG. 30 is an exploded perspective view of another embodiment of an exemplary LED lamp including an embodiment of the aromatic structure of the invention.

While the aromatic structure may be other than the trim ring, making the trim ring 820 the aromatic structure is advantageous in that the trim ring is typically removable and replaceable in existing light fixtures such that a mounting structure already exists for removably mounting the trim ring to the light fixture. For example referring to FIG. 30 another embodiment of a light fixture is shown comprising a two part housing 902a, 902b for retaining the LED assembly/light engine 904. The LED assembly 904 comprises at least one and typically a plurality of LEDs (not shown). The lamp electronics for powering and controlling operation of the LEDs form part of the LED assembly. Suitable electrical conductors 914 such as wiring or the like connect the LED assembly to a power source. A mounting structure 908 for mounting the light fixture to the ceiling or the ceiling support structure such as joists may also be provided. Further these lamps also typically comprise optical elements 918 for color mixing, shaping and directing the light emitted from the lamp. The trim ring 920 typically comprises an annular shaped ring that covers the housing and the housing/ceiling interface where light is emitted through the opening 922 of the trim ring 920. The trim ring 920 may also include optical elements for shaping or treating the light. For example the trim ring 920 may have a reflector surface 924, lens (not shown) or the like. Because the trim ring 920 is used as a decorative part it is typically installed to the housing separately after the light fixture is installed in the lamp. In the embodiment of FIG. 30 the trim ring includes spring clips 926 that releasably engage the housing portion 902b. The trim ring 920 comprises the aromatic structure as previously described where the trim ring 920 comprises a plastic material infused with an aromatic substance. Because the trim ring contacts or is in close proximity to the heat conducting portions of the light fixture such as housing 902a, 902b the heat generated by the lamp heats the aromatic structure to facilitate release of the scent.

Figure 31:
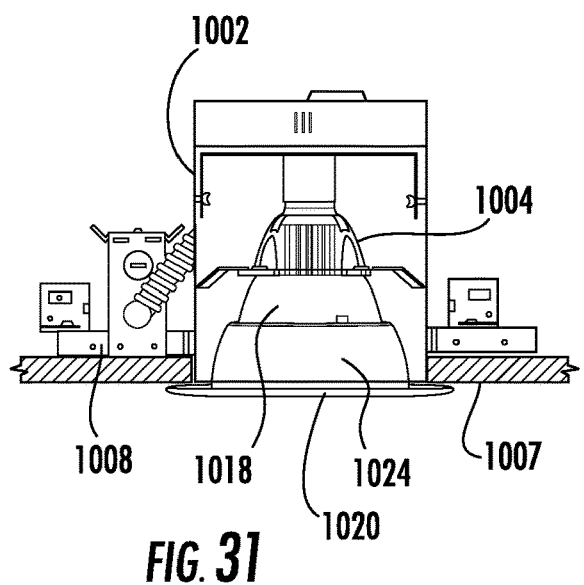
FIG. 31 is a section view of an embodiment of an exemplary LED lamp including an embodiment of the aromatic structure of the invention.

Another embodiment of a light fixture is shown in FIG. 31 and comprises a two part housing 1002 for retaining the LED assembly/light engine 1004. The LED assembly comprises at least one and typically a plurality of LEDs (not shown). The lamp electronics for powering and controlling operation of the LEDs form part of the LED assembly or be contained off the LED assembly. A mounting structure 1008 for mounting the light fixture to the ceiling 1007 or the ceiling support structure such as joists may also be provided. Further these lamps also typically comprise optical elements such as a reflector 1018 for color mixing, shaping and directing the light emitted from the lamp. The trim ring 1020 typically covers the housing and the housing/ceiling interface where light is emitted through the central opening. The trim ring 1020 may also include optical elements for shaping or treating the light. For example the trim ring 1020 may have a reflector surface 1024, lens (not shown) or the like. Because the trim ring 1020 is used as a decorative part it is typically installed to the housing separately after the light fixture is installed in the lamp. In the embodiment of FIG. 31 the trim ring is screwed onto the reflector 1018. The trim ring 1020 comprises the aromatic structure as previously described where the trim ring 1020 comprises a plastic material infused with an aromatic substance. Because the trim ring contacts or is in close proximity to the heat conducting portions of the light fixture such as housing 1002 and reflector 1018 the heat generated by the lamp heats the aromatic structure to facilitate release of the scent Although specific embodiments have been shown and described herein, those of ordinary skill in the art appreciate that any arrangement, which is calculated to achieve the same purpose, may be substituted for the specific embodiments shown and that the disclosure has other applications in other environments. This application is intended to cover any adaptations or variations of the present disclosure. The following claims are in no way intended to limit the scope of the disclosure to the specific embodiments described herein.

The invention claimed is:

1. An LED lamp comprising:
a LED assembly comprising at least one LED operable to emit ight when energized through an electrical path;
a heat sink structure thermally coupled to the LED assembly, the heat sink structure comprising a heat dissipating portion that is exposed to an exterior of the lamp for dissipating heat to the ambient environment;
an aromatic structure comprising a plastic infused with an aromatic material that is mounted on the exterior of the lamp and is positioned at least partially over the heat dissipating portion and is in thermally coupled to the heat sink structure such that the aromatic structure is heated by the heat dissipated from the heat sink structure to facilitate the emission of a scent from the aromatic structure.

2. The LED lamp of claim 1, wherein the aromatic structure is removably mounted to the lamp.

3. The LED lamp of claim 1, wherein the aromatic structure is removably attached to the lamp using at least one of a snap-fit connector, a friction fit, an adjustable strap, a screw connection and a spring clip.

4. The LED lamp of claim 1, wherein the aromatic structure comprises apertures allowing the heat sink structure access to the ambient environment.

5. The LED lamp of claim 1, wherein the aromatic structure is permanently attached to the heat sink structure.

6. The LED lamp of claim 1, wherein the aromatic structure is part of the heat sink structure.

7. The LED lamp of claim 1, wherein the aromatic structure is part of a housing.

8. An LED lamp comprising:
a LED assembly comprising at least one LED operable to emit light when energized through an electrical path;
a heat sink structure thermally coupled to the LED assembly comprising a heat dissipating portion having an exterior surface that is exposed to an exterior of the lamp for dissipating heat to the ambient environment;
an aromatic structure mounted on the exterior of the lamp and having an interior surface, the interior surface contacting the exterior surface of the heat dissipating portion such that the aromatic structure is heated by the heat dissipated from the heat sink structure to facilitate the emission of a scent from the aromatic structure.

9. The lamp of claim 8, wherein the aromatic structure comprises a plastic infused with an aromatic material.

10. The LED lamp of claim 8, wherein the aromatic structure is removably mounted to the lamp.

11. The LED lamp of claim 10, wherein the aromatic structure is removably attached to the lamp using at least one of a snap-fit connector, a friction fit, an adjustable strap, a screw connection and a spring clip.

12. The LED lamp of claim 8, wherein the aromatic structure comprises apertures allowing the heat sink structure access to the ambient environment.

13. The LED lamp of claim 8, wherein the aromatic structure is permanently attached to the lamp.

14. The LED lamp of claim 8, wherein the aromatic structure is molded to the heat sink structure.

15. The LED lamp of claim 8, wherein the aromatic structure comprises a trim ring.

16. An aromatic structure for an LED lamp comprising:
a shell configured to fit at least partially over an exposed portion of a heat sink of a LED lamp, the shell comprising a plastic infused with an aromatic material.

17. The LED lamp of claim 16, wherein the shell comprises at least one of a snap-fit connector, an adjustable strap, a screw connection and an elastic strap.

18. An aromatic structure for an LED lamp comprising:
an annular trim ring configured to attach to a housing of a LED lamp such that it covers an exposed portion of the housing, the trim ring comprising a plastic infused with an aromatic material.

19. The LED lamp of claim 18, wherein the trim ring comprises at least one of a spring clip, screw and deformable connector.

* * * * *

UNITED STATES PATENT AND TRADEMARK OFFICE
CERTIFICATE OF CORRECTION

| | | |
|---|---|---|
| PATENT NO. | : 10,260,685 B2 | Page 1 of 1 |
| APPLICATION NO. | : 15/427568 | |
| DATED | : April 16, 2019 | |
| INVENTOR(S) | : Bernard et al. | |

It is certified that error appears in the above-identified patent and that said Letters Patent is hereby corrected as shown below:

In the Claims

Column 18, Line 10, Claim 1: Please correct "ight" to read -- light --

Column 18, Line 18, Claim 1: Please correct "is in thermally coupled" to read -- is thermally coupled --

Signed and Sealed this
Third Day of September, 2019

Andrei Iancu
*Director of the United States Patent and Trademark Office*